US009415019B2

(12) United States Patent
Alonso Fernández et al.

(10) Patent No.: US 9,415,019 B2
(45) Date of Patent: Aug. 16, 2016

(54) NANOCAPSULES WITH A POLYMER SHELL

(75) Inventors: María José Alonso Fernández, Santiago de Compostela (ES); Dolores Torres Lopez, Santiago de Compostela (ES); Gustavo Rivera Rodriguez, Santiago de Compostela (ES); Felipe Andrés Oyarzún Ampuero, Santiago de Compostela (ES); Giovanna Lollo, Santiago de Compostela (ES); Teresa Gonzalo Lázaro, Santiago de Compostela (ES); Marcos García Fuentes, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 0 days.

(21) Appl. No.: 13/979,092

(22) PCT Filed: Jan. 9, 2012

(86) PCT No.: PCT/ES2012/000008
§ 371 (c)(1),
(2), (4) Date: Sep. 30, 2013

(87) PCT Pub. No.: WO2012/095543
PCT Pub. Date: Jul. 19, 2012

(65) Prior Publication Data
US 2014/0023703 A1    Jan. 23, 2014

(30) Foreign Application Priority Data
Jan. 10, 2011  (ES) .................................. 201130015

(51) Int. Cl.
*A61K 9/51*     (2006.01)
*B82Y 5/00*    (2011.01)
(Continued)

(52) U.S. Cl.
CPC ............. *A61K 9/5107* (2013.01); *A61K 9/5192* (2013.01); *A61K 31/337* (2013.01);
(Continued)

(58) Field of Classification Search
None
See application file for complete search history.

(56) References Cited

U.S. PATENT DOCUMENTS 4,670,185 A * 6/1987 Fujiwara et al. ................. 516/57
5,559,157 A * 9/1996 Kawashima et al. .......... 514/777
(Continued)

FOREIGN PATENT DOCUMENTS

BR        PI0803473 A2    6/2010
WO    WO 2009/087678 A2    7/2009

OTHER PUBLICATIONS

W Abdelwahed, G Degobert, S Stainmesse, H Fessi. "Freeze-drying of nanoparticles: Formulation, process and storage considerations." Advanced Drug Delivery Reviews, vol. 58, 2006, pp. 1688-1713.*
(Continued)

*Primary Examiner* — Isaac Shomer
(74) *Attorney, Agent, or Firm* — Monahan & Company, LLC; Timothy J. Monahan

(57) ABSTRACT

The invention relates to a system for administering active ingredients, including nanocapsules comprising an oil, a cationic surfactant and a polymer selected from the group consisting of polyglutamic acid (PGA), polyglutamic-polyethyleneglycol acid (PGA-PEG), hyaluronic acid (HA) and polyasparagine (PAsn) or a combination of same and, optionally, an active ingredient, with the condition that when the polymer includes polyglutamic acid or polyglutamic-polyethyleneglycol acid (PGA-PEG) the active ingredient is not a didemnin or a tamandarin. The invention also relates to methods for obtaining said nanocapsule system, the pharmaceutical compositions thereof and the use of same in medicine.

21 Claims, 19 Drawing Sheets

(51) Int. Cl.
  *A61K 31/337* (2006.01)
  *A61K 45/06* (2006.01)
  *A61K 31/713* (2006.01)
  *A61K 47/26* (2006.01)
  *A61K 9/19* (2006.01)

(52) U.S. Cl.
  CPC .............. *A61K31/713* (2013.01); *A61K 45/06* (2013.01); *B82Y 5/00* (2013.01); *A61K 9/19* (2013.01); *A61K 9/5146* (2013.01); *A61K 9/5153* (2013.01); *A61K 47/26* (2013.01); *Y10S 977/773* (2013.01); *Y10S 977/906* (2013.01)

(56) References Cited

U.S. PATENT DOCUMENTS

| | | | |
|---|---|---|---|
| 5,612,058 | A * | 3/1997 | Schutz et al. .................. 424/489 |
| 6,007,826 | A * | 12/1999 | Benita et al. .................. 424/401 |
| 6,365,706 | B1 * | 4/2002 | Ma ............................ C05C 9/00 525/418 |
| 6,593,308 | B2 * | 7/2003 | Szoka, Jr. ......................... 514/54 |
| 8,114,842 | B1 * | 2/2012 | Sung .................... A61K 9/0019 514/15.6 |
| 2002/0192280 | A1 * | 12/2002 | Hunter et al. .................. 424/465 |
| 2004/0047891 | A1 * | 3/2004 | Glozman et al. .............. 424/423 |
| 2004/0254352 | A1 * | 12/2004 | Metselaar ............ A61K 9/1271 530/359 |
| 2006/0035901 | A1 * | 2/2006 | Hanson et al. ................. 514/251 |
| 2006/0153923 | A1 * | 7/2006 | Fernandez et al. ............ 424/489 |
| 2006/0188578 | A1 * | 8/2006 | Fernandez .......... A61K 9/0014 424/489 |
| 2007/0036829 | A1 * | 2/2007 | Yu et al. ........................ 424/400 |
| 2007/0099856 | A1 * | 5/2007 | Gumerlock ...................... 514/34 |
| 2007/0237831 | A1 * | 10/2007 | Sung .................... A61K 9/5146 424/490 |
| 2007/0293501 | A1 * | 12/2007 | Boyd .................. C07D 213/73 514/252.1 |

OTHER PUBLICATIONS

M Mansour, S Mansour, ND Mortada, SS Abd ElHady. "Ocular Poloxamer-Based Ciprofloxacin Hydrochloride In Situ Forming Gels." Drug Development and Industrial Pharmacy, vol. 34, 2008, pp. 744-752.*

E Fattal, A Bochot. "Ocular delivery of nucleic acids: antisense oligonucleotides, aptamers and siRNA." Advanced Drug Delivery Reviews, vol. 58, 2006, pp. 1203-1223.*

S Barbault-Foucher, R Gref, P Russo, J Geuchot, A Bochot. "Design of poly-e-caprolactone nanospheres coated with bioadhesive hyaluronic acid for ocular delivery." Journal of Controlled Release, vol. 83, 2002, pp. 365-375.*

I Yenice, MC Mocan, E Palaska, A Bochot, E Bilensoy, I Vural, M Irkec, AA Hincal. "Hyaluronic acid coated poly-e-caprolactone nanospheres deliver high concentrations of cyclosporine A into the cornea." Experimental Eye Research, vol. 87, 2008, pp. 162-167.*

MA Woodruff, DW Hutmacher. "The return of a forgotten polymer—Polycaprolactone in the 21st century." Progress in Polymer Science, vol. 35, 2010, pp. 1217-1256.*

International Search Report and Written Opinion for PCT/ES2012/000008, mailed May 28, 2012.

International Preliminary Report on Patentability for PCT/ES2012/000008, mailed Jul. 18, 2013.

Yenice et al., Hyaluronic acid coated poly-epsilon-caprolactone nanospheres deliver high concentrations of cyclosporine A into the cornea. *Exp Eye Res.* Sep. 2008;87(3):162-7. doi: 10.1016/j.exer.2008.04.002. Epub Apr. 12, 2008.

* cited by examiner

NANOCAPSULES WITH A POLYMER SHELL

RELATED APPLICATIONS

The present application is a national stage filing under 35 U.S.C. §371 of international PCT patent application, PCT/ES2012/000008, filed Jan. 9, 2012, which claims priority to Spanish patent application, P201130015, filed Jan. 10, 2011, each of which is incorporated herein by reference.

FIELD OF THE INVENTION

The present invention relates to a system for the administration of active ingredients comprising nano-sized nanocapsules, as well as to pharmaceutical compositions comprising the same and manufacturing methods thereof.

BACKGROUND OF THE INVENTION

The incorporation of active ingredients inside nano-sized systems has helped to solve formulation constraints of these molecules, further increasing their therapeutic potential. Improvements in solubility, protection against degradation or increased penetration of the active ingredients are some of the advantages of active molecule nanoencapsulation. Likewise, it is also known that the capacity of these systems to cross external barriers and access the interior of the organism, both depends on their size and on their composition. Small-sized particles will increase the degree of transport with respect to those of larger size: nanosystems, with a diameter of less than 1 µm, meet this criteria.

Polyglutamic Acid (PGA)

Polyglutamic acid (PGA) is a hydrophilic and biodegradable polymer made of negatively charged glutamic acid units. Due to its biological properties such as non-toxicity, its non-immunogenicity and biocompatibility, this polymer has been regarded as an important biomaterial for the development of new formulations for drug delivery (Buescher & Margaritis, Crit RevBiotech 2007).

For example, the use of polyglutamic acid is widely reported for the formation of drug-polymer complexes of interest in cancer treatment, being some formulations in advanced development stages. Such is the case of Xyotax, a formulation consisting of conjugates between poly-L-glutamic acid and cytostatic agent paclitaxel, which is currently in Phase 3 clinical trials. Also this polymer has been used to design formulations for administering other antitumor agents such as doxorubicin (Shih et al., 2004).

Furthermore, US 2006/0246096 reports the use of polyglutamic acid in the formulation of drug delivery systems, being used as shell in formulations for the carrying genetic material from them.

Another type of delivery system developed from polyglutamic acid are the nanoparticles, as disclosed in US 2005/0238678 and U.S. Pat. No. 6,326,511.

On the other hand, polyglutamic acid has also been conjugated to polyethylene glycol (PEG) in order to effect changes on the surface of nanometric systems, attempting to provide greater stability of colloidal systems. Such modification with PEG also minimizes recognition of nanosystems by proteins and cells of the reticuloendothelial system, thus increasing the circulation time thereof.

The effect of conjugation of the PEG with polyglutamic acid has been investigated in US 2003/0170201, which assesses the potential of the complexes formed from such polymer for releasing of cytostatic drugs.

Hyaluronic Acid (HA)

Hyaluronic acid (HA) is a naturally occurring polymer. More specifically it is a glycosaminoglycan present in the extracellular matrix of connective tissues such as the subcutaneous and cartilaginous; it is also found in the vitreous body of the eye and synovial fluid of articular cavities. It is a polymer capable of interacting with CD44 and RHAMM endogenous receptors which are located at the cell surface in practically all cells of the body except red blood cells. The interaction of hyaluronic acid with these receptors allows regulating certain physiological processes such as mobility and cell proliferation. Due to these properties, hyaluronic acid has therapeutic use, as it plays an important role in processes such as morphogenesis and embryo development, cancer and inflammation. Moreover, due to said properties, hyaluronic acid is used to promote epithelial healing. Proof of this biological activity are numerous jobs that include hyaluronic acid as active biomolecule, were we can mention those described by Sand et al. (Acta Ophthalmol. 67, 1989, 181-183), where hyaluronic acid is applied in the treatment of keratoconjunctivitis sicca, by Nishida et al. (Exp. Eye Res 53, 1991, 753-758), wherein it is applied to corena as healing agent and by Blanco et al. (Clin. Exp Rheumatol. 22 (3) 2004, 307-12), where the polymer is applied for the treatment of osteoarthritis, among others. Additionally, hyaluronic acid and its derivatives, under various forms of presentation, have been the subject of numerous patent documents wherein they are presented as active molecules. At this point it should be noted patent application WO 96/06622, which claims the use of hyaluronic acid and derivatives, alone or in combination with another therapeutic agent, to modulate cellular activity of those tissues and cells which express on their surface hyaluronic acid receptors, and thus treat or prevent inflammatory processes, fibrosis or oncogenesis. U.S. Pat. No. 6,383,478 protects a delivery system consisting of microparticles, nanoparticles or films which incorporate hyaluronic acid as possible active molecule to promote angiogenesis.

On the other hand, hyaluronic acid has also been the subject of numerous studies proposing its use as a biomaterial-excipient used in the development of drug delivery systems. The interest is due to the fact that it is a biodegradable polymer, biocompatible, non-immunogenic, mucoadhesive and selective affinity for receptors such as CD44. Regarding the antecedents focused on obtaining nanometric formulations using hyaluronic acid as biomaterial-excipient the following, among many other, can be mentioned:

- U.S. Patent Application 2007/0224277, which describes the preparation of hyaluronic acid nanoparticles formed by covalent crosslinks.
- U.S. Patent Application 2003/0166602 A1, which discloses the preparation of different formulations with a hyaluronic acid-modified lipid, and that can hold active ingredients with anticancer activity or other therapeutic or diagnostic agents.
- Patent Application WO 2004/112758 A1, which describes the preparation of nanoparticles in an aqueous medium containing hyaluronic acid which are formed by ionic interaction between the same, other polymers of complementary charge and in the presence of the ionic type crosslinking agent.
- Luo and Prestwich (Bioconjugate Chem 10, 1999, 755-763) synthesized a conjugate between hyaluronic acid and the anticancer agent Taxol, and whose cytotoxic activity is higher and more selective than that obtained only with Taxol in breast, colon and ovarian cell lines over expressing the receptor CD44.

Yenice et al (Experimental Eye Research 2008, 87 (3), 162-7) and Barbaultfoucher et al (Journal of Controlled Release 2002, 83, 365-375) describe nanospheres of poly-ε-caprolactone coated with hyaluronic acid as system for ocular drug delivery.

Polyasparagine (PAsn)

Since it intervenes directly in the synthesis of proteins and DNA, and the main source is in the diet, L-asparagine is described in the literature as an essential amino acid for growth and development of all cell types.

L-asparagine is currently one of the more and better used strategies for cancer treatment, being commercialized a formulation that includes the enzyme required for its degradation. When administering this enzyme and achieve its deposition in the tumor periphery, a reduction in the concentration of the amino acid is obtained, causing deficiencies thereof; the cells are then prevented from synthesizing DNA and other proteins essential for survival. Such formulation is called Oncaspar™ or Elspar™, L-asparaginase being the enzyme responsible for this degradation.

Cancer cells in advanced stages of metastasis, especially leukemia, exhibit high affinity for asparagine due to a high recognition in the surface, caused by their rapid reproduction. Cancerous cells cannot effectively meet their basic needs for this amino acid, which in many cases leads to the migration of these cells in search of higher concentrations of this amino acid towards the tumor periphery. Such recognition and necessity has been recently used as an alternative for the treatment of many cancers metastatic stage. There have been numerous studies based on asparagine of nanoscale systems such as polymeric micelles or liposomes coated polymeric derivatives.

Said studies have shown great potential for the development of nanosystem based on polyaminoacids based on asparagine, such as polyasparagine (PAsn) or polyhydroxyethylasparagine. Moreover, combined with the specificity conferred by the surface recognition asparagine, polymers based on this aminoacid have shown, structural and physicochemical properties similar to PEG, which provides the drug an improved half-life in progress, and a remarkable improvement in pharmacokinetics and biodistribution.

In studies related to polyasparagine, Storm and colleagues (Metselaar, Bruin et al. 2003; Garcion, Lamprecht et al. 2006; Romberg, Kettenes-Van Den Bosch et al. 2006; Romberg, Metselaar et al. 2007; Romberg Oussoren et al. 2007; Romberg Oussoren et al. 2007; Romberg Oussoren et al. 2007; Romberg, Flesch et al. 2008; Romberg, Hennink et al. 2008) evaluated the pharmacokinetics of two different types of liposomes coatings by varying the coating polymer, comparing polyhydroxyethylasparagine with PEG. The results favored polyhydroxyethylasparagine presenting better pharmacokinetics and a longer circulation time at low doses and repeated administration.

From the information presented above, the potential and interest of the aforementioned compounds—polyglutamic acid and its copolymer with PEG, hyaluronic acid, and polyasparagine—as biomaterial-excipient in the development of new delivery systems is evident. Particularly, it would be desirable to obtain certain applications of stable nanosystems, suitable to encapsulate and protect molecules of different characteristics, and which would also present good adsorption and internalization properties into the desired biological surfaces.

SUMMARY OF THE INVENTION

The authors of the present invention have developed a nanocapsular system easily obtained using different experimental procedures, wherein the nanocapsules comprise a polymer, an oil and a cationic surfactant. These nanocapsular systems enable an effective partnership of lipophilic active ingredients and as well as hydrophilic ones. The small size of said nanocapsules (diameter less than 1 μm) allows passage through biological barriers and internalized by cells. Also, the presence of a polymeric shell, in addition to conferring greater stability to the nanocapsules, provides various beneficial characteristics depending on each particular type of shell.

Thus, in a first aspect the invention is directed to a system for the administration of active ingredients comprising nanocapsules which comprise an oil, a cationic surfactant and a polymer selected from the group consisting of polyglutamic acid (PGA), polyglutamic-polyethyleneglycol acid (PGA-PEG), hyaluronic acid (HA) and polyasparagine (PAsn) or a combination thereof, and optionally an active ingredient, with the proviso that when said nanocapsules system includes polyglutamic acid or polyglutamic-polyethyleneglycol acid (PGA-PEG), then the active ingredient is not a didemnin or tamandarin.

Furthermore, the nanocapsules of the invention may also comprise optionally other components such as a water-soluble surfactant an oil-soluble surfactant, or both.

In another aspect, the invention relates to a pharmaceutical composition comprising the previously defined system.

Furthermore, the invention relates to the use of said system in the preparation of a medicament.

In a particular embodiment, said use relates to the treatment of cancer.

In a further aspect, the invention is directed to a process for obtaining the above defined system (referred to in the examples solvent diffusion process in one stage), comprising:
 a) preparing an aqueous solution comprising a polymer selected from the group consisting of polyglutamic acid (PGA), polyglutamic-polyethyleneglycol acid (PGA-PEG), hyaluronic acid (HA) and polyasparagine (PAsn) or a combination thereof, and optionally a water-soluble surfactant;
 b) preparing an organic solution comprising an oil and a cationic surfactant, and optionally an oil-soluble surfactant;
 c) mixing under stirring the solutions prepared in steps a) and b), spontaneously obtaining the nanocapsules, and
 d) optionally, wholly or partially evaporating to constant volume the organic solvents from the mixture obtained in the previous stage.

According to particular embodiments, the encapsulation of a lipophilic active ingredient (hydrophobic) or amphiphilic is carried out by adding it in step b). The active ingredients of hydrophilic nature can be added in step a) of the process or at a stage later than stage d) through a process of incubation.

In another aspect, the invention is directed to a process for obtaining the above defined systems, comprising coating a nanoemulsion, at least constituted by an oil, a cationic surfactant, optionally an oil-soluble surfactant and an aqueous phase optionally comprising a water-soluble surfactant, through a process of incubation with an aqueous solution of polyglutamic acid (PGA), polyglutamic-polyethyleneglycol acid (PGA-PEG), hyaluronic acid (HA), polyasparagine (PAsn) or a mixture thereof.

According to a particular embodiment, the above process further comprises adding an active ingredient. As defined above, when the polymer is polyglutamic acid or polyglutamic-polyethyleneglycol acid (PGA-PEG), then the active ingredient is not a didemnin or tamandarin.

According to a more particular embodiment, if the active ingredient has a lipophilic character, said active ingredient is added in the formation of the nanoemulsion, preferably dissolved in ethanol.

DETAILED DESCRIPTION OF THE INVENTION

Figure 1A:
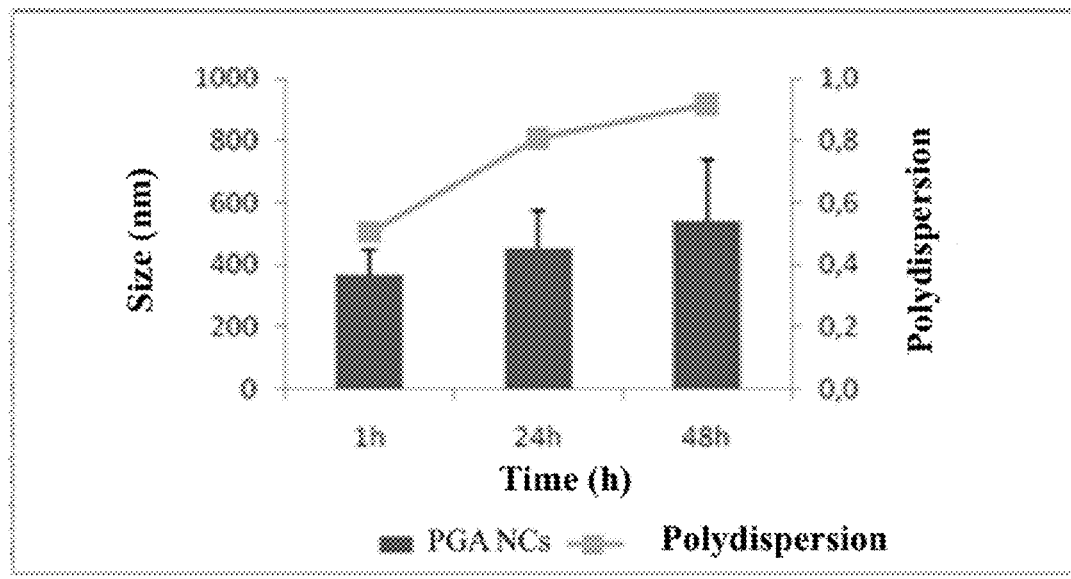
FIG. 1: Evolution of particle size and polydispersity of polyglutamic nanocapsules (1.a) and polyglutamic-polyethyleneglycol acid (1b) at 37° C. for a period of 48 h.

The present invention is directed to the design and development of nanocapsules for the administration of active ingredients, wherein the nanocapsules of the system have a diameter less than 1 μm and is characterized by comprising (a) a shell of a polymer selected from the group consisting of polyglutamic acid, polyglutamic-polyethyleneglycol acid, hyaluronic acid, polyasparagine, or a combination thereof and (b) a core which in turn comprises an oil and a cationic surfactant. The nanocapsules of the invention also preferably comprise at least one active ingredient, with the proviso that when the polymer is polyglutamic acid or polyglutamic-polyethyleneglycol acid (PGA-PEG), then the active ingredient is not a didemnin or tamandarin.

Nanocapsules: Nature and Size

The advantage of nanocapsule systems with respect to emulsion systems is the presence of a polymer coating the oily cores that may confer greater stability and protection against aggregation, a change in the drug release profile of the drug associated, an increased cellular internalization and specific interaction with certain cell types.

Compared with other systems such as liposomes or nanoparticles which are generally conditioned to a limited drug loading, the nanocapsules have a greater charging possibility, in particular of lipophilic drugs, due to the presence of the oily core. Another major advantage of the nanocapsules is the ability to combine drugs of different nature, a lipophilic drug being encapsulated in the core and a hydrophilic drug associated to the shell; also the shell provides stability, protection and specificity.

These systems also have advantages over larger ones (microparticles, pellets, films, sponges . . . ) in their biological applications. In fact, it is known that the interaction of a drug delivery system with a biological surface is highly conditioned by its size. Thus, the nanocapsules are able to cross mucosa and be internalized by the cells acting as drug transport systems, whilst microparticles do not have that capability. Similarly, the biodistribution of these systems is highly conditioned by size. The knowledge generated in recent years in the world of nanomedicine and drug delivery nanosystems has allowed to set a clearly defined frontier between nanometric systems (which have a sub-micron size eg. Nanoparticles and nanocapsules) and micrometer systems (microparticles and microcapsules). Besides behavioral differences in their ability to be internalized by cells and overcome complex biological barriers, in the case of formulations intended for intravenous administration of antitumor drugs the nanosize of the delivery systems is essential to prevent clogging of the blood capillaries. It is also known that the chances of nanosystems reaching tumor tissue are strictly related to their size and also by the hydrophilicity of its surface.

The nanocapsules of the system of the present invention have a mean diameter less than 1 μm, therefore responding to the definition of nanosystem, colloidal system formed from polymers with a size less than 1 μm, namely, which have a size of between 1 and 999 nm, preferably between 30 and 500 nm. The size of the nanocapsules is influenced mainly by the composition and formation conditions, and can be measured using standard procedures known to those skilled in the art and described, for example, in the experimental part below. The size thereof does not significantly vary when changing the ratio of shell compound in the formulation, in all cases obtaining nano-sized systems.

It is also important to note the difference between the systems of nanocapsules and "complex". The term "complex" is understood as the nanostructure formed by the interaction of polyelectrolytes or by polyelectrolytes and surfactants of opposite charge. Nanocapsules systems of the present invention differ from paclitaxel-polyglutamic complexes (U.S. 2003170201) or hyaluronic acid (Kim et al. J. Gene Med (2009) 11:791) because it is a nanocapsular transport system of the reservoir type, which core can accommodate a large number of molecules having more or less affinity for lipids (encapsulation) and whose shell can incorporate hydrophilic molecules having an affinity for the same (adsorption). These features allow to maintain the integrity and functionality of the nanostructure, and provide greater stability in the presence of biological fluids.

Components
Polyglutamic Acid (PGA) and Polyglutamic-Polyethyleneglycol Acid (PGA-PEG)

As mentioned in the background, polyglutamic acid and its conjugated with PEG are very interesting biomaterials in designing delivery systems of active molecules.

As used herein, PGA includes water soluble salts of PGA, as the ammonium salt of PGA and metal salts such as lithium salt, sodium salt, potassium salt, magnesium salt, etc.

Furthermore, in one embodiment, the PGA form is selected from poly-D-glutamic acid, poly-L-glutamic acid, poly-D, L-glutamic acid, poly-α-glutamic acid, poly-α-D-glutamic acid, poly-α-L-glutamic acid, poly-α-D, L-glutamic acid, poly-γ-glutamic acid, poly-γ-D-glutamic poly-γ-L-glutamic acid and poly-γ-D, L-glutamic acid, and mixtures thereof. In another embodiment, the preferred form of PGA is poly-L-glutamic acid, and most preferred is the sodium salt of poly-L-glutamic acid. In another embodiment, the preferred form of PGA is poly-α-glutamic acid, and most preferred is the sodium salt of poly-α-glutamic acid.

Furthermore, the nanocapsules of the invention may be formed from water-soluble derivatives of PGA or PGA-PEG, where PGA is substituted at one or more available positions, for example amine groups and/or carboxylic acid, with one or more appropriate groups.

Suitable derivatives of PGA and PGA-PEG derivatives include poly (alkylglutamine) and derivatives of PEG-poly (alkylglutamine) such as poly (N-2-(2'-hydroxyethoxy) ethyl-L-glutamine) (PEEG), PEG-PEEG, poly (N-3-(hydroxypropyl)-L-glutamine) (PHPG), PEG-PHPG, poly (N-2-(hydroxyethyl)-L-glutamine) (PHEG) PEG-PHEG, poly (γ-benzyl-L-glutamate) (pBG), PEG-pBG, poly (γ-trichloroethyl-L-glutamate) (pTCEG) pTCEG-PEG, poly(dimethylaminoethyl-L-glutamine) (pDMAEG), PEGp-DMAEG, poly(pyridinoethyl-L-glutamine) (pPyAEG), PEG-pPyAEG, poly (aminoethyl-L-glutamine) (pAEG), PEG-pAEG, poly (histamine-L-glutamine) (pHisG), PEG-pHisG, poly (agmatine-L-glutamine) (pAgmG) and PEG-pAgmG, and mixtures thereof (Hoste et al. J. Control. Release, 2000, 64, 53-61; Dekie J. Control. Release, 2000, 65, 187-202; Dubruel et al. Biomacromolecules, 2003, 4, 1168-1176). In any case, anyone skilled in the art is able to identify the modifications which can be performed in PGA to give water-soluble derivatives thereof.

The presence of a shell based on pegylated polymer gives nanocapsules greater stability in plasma and an increase in the residence time in the body, facilitating arrival at the therapeutic target. Thus, the surface modification of nanostructures with PEG chains is capable of reducing their uptake by the mononuclear phagocyte system through what is termed the stealth system or long circulation systems (Park J H et al, 2008). Thanks to its prolonged presence in the bloodstream, it was observed that these systems possessed greater possibility of reaching target organs. This modification resulted interest for transport and guidance of cytostatic drugs, which target tissue typically present hypervascularization and increased permeability of blood vessels.

Polyethylene glycol (PEG), in its most common form, is a polymer of formula (I):

$$H-(O-CH_2-CH_2)_p-OH \qquad (I)$$

where p is an integer representing the PEG polymerization degree.

For the formation of the polyglutamic-polyethyleneglycol acid conjugated it is necessary to use a modified PEG in which one or both terminal hydroxyl groups are modified.

Among the modified PEG that can be used to obtain PGA-PEG conjugates those having the formula (II) can be included:

$$X_1-(O-CH_2-CH_2)_p-X_2 \qquad (II)$$

wherein:

$X_1$ is hydrogen or a hydroxyl protecting group blocking the OH function for subsequent reactions. The protective groups of hydroxyl radicals are widely known in the art; representative protecting groups (already including the oxygen to be protected) are silyl ethers such as trimethylsilyl ether, triethylsilyl ether, tertbutyldimethylsilyl ether, tert-butyldiphenylsilyl ether, triisopropylsilyl ether dietilsopropilsilil ether texildimetilsilil ether, triphenylsilyl ether, di-tert-butylmethylsilyl ether, alkyl ethers such as methyl ether, tert-butyl ether, benzyl ether, p-methoxybenzyl ether, 3,4-dimethoxybenzyl ether, trityl ether, allyl ether; alkoxymethyl ethers such as methoxymethyl ether, 2-methoxyethoxymethyl, benzyloxymethyl ether, p-metoxibenciloximetil ether, 2-(trimethylsilyl) ethoxymethyl ether, tetrahydropyranyl ether and related ethers; methylthiomethyl ether, esters such as acetate ester, benzoate ester, ester pivalate ester, methoxyacetate, chloroacetate ester, levulinate ester, carbonates such as benzyl carbonate, p-nitrobenzyl carbonate, tert-butyl carbonate, 2,2,2-trichloroethyl carbonate, 2-(trimethylsilyl) ethyl, allyl carbonate. Other examples of hydroxyl protecting groups can be found in reference books such as "Protective Groups in Organic Synthesis" by Greene and Wuts, John Wiley & Sons, Inc., New York, 1999. In a preferred embodiment, the protecting group is an alkyl ether, preferably it is methyl ether.

$X_2$ is a bridge group allowing the anchoring to polyglutamic acid groups and to groups of the derivatives thereof. Alternatively $X_1$ may also be a group allowing the anchoring with other PGA and derivatives thereof.

Preferably, the PEGs are attached to PGA and derivatives via amine groups and/or carboxylic acid of the latter. Pegylation of the polymers can be performed using any suitable method available in the art (as described in Veronese et al. DDT, 2005, 10 (21), 1451-1458, Nishiyama et al. Cancer Research 2003, 63, 8977-8983; Cabrera et al. J. Control. Release, 2005, 101, 223-232, U.S. 2003/0170201).

These polymers are available in a variety of molecular weights, and the appropriate molecular weight for a given use is readily determined by a skilled artisan. Thus, for example, a suitable molecular weight of PGA in PGA and PGA-PEG polymer may be between about 1 kDa and about 100 kDa, preferably between about 5 kDa and about 80 kDa, more preferably between about 10 kDa and about 50 kDa, and most preferably about 10 kDa, about 15 kDa, about 20 kDa, about 25 kDa, about 30 kDa and about 35 kDa.

A molecular weight PEG in PGA-PEG polymers and water soluble derivatives thereof can be between about 1 kDa and about 50 kDa, preferably between about 2 kDa and about 40 kDa, more preferably between about 3 kDa to about 30 kDa, and still more preferably about 4 kDa, about 5 kDa, about 6 kDa, about 7 kDa, about 8 kDa, about 10 kDa, about 15 kDa, about 20 kDa, about 21 kDa, about 22 kDa, about 23 kDa, about 24 kDa, about 25 kDa and about 30 kDa.

Additionally, PGA-PEG polymers and water soluble derivatives thereof are available in a variety of degrees of pegylation, and pegylation degree appropriate for a given use is readily determined by a skilled artisan. This pegylation degree is defined as the percentage of functional groups or functional groups PGA or PGA derivatives that are functionalized with PEG. Therefore, suitable pegylation grades in PGA-PEG polymers and water-soluble derivatives thereof can be between about 0.1% and about 10%, preferably about 0.2% and about 5%, more preferably between about 0.5% and about 2%, and most preferably about 0.5%, about 0.6%, about 0.7%, about 0.8%; about 0.9%, about 1%, about 1.1%; about 1.2%, about 1.3%, about 1.4%; about 1.5%, about 1.6%, about 1.7%; about 1.8%; about 1.9%, about 2%.

Moreover, the proportion of PEG in the PEG-PGA polymers and water-soluble derivatives thereof can be between about 10% and 90% (w/w) with respect to the total weight of the polymer, preferably between about 15% and 80%, more preferably between about 20% and 70%, and most preferably about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58% and about 60%.

Hyaluronic Acid (HA)

The presence of hyaluronic acid on the surface of the nanocapsules gives them the ability to adhere to mucosal surfaces due to its known mucoadhesive property. On the other hand, they have great potential to achieve active vihiculation towards cells with rapid growth and CD44 receptor overexpression allowing them to form tissues; a clear example of such cell behavior is observed in several types of cancer cells.

As used herein, HA includes water-soluble salts and water-soluble derivatives of HA. In a particular embodiment, the hyaluronic acid salt is selected from the group consisting of sodium, potassium, magnesium, calcium and zinc salts. A preferred form of hyaluronic acid salt is its sodium salt.

Polyasparagine (PAsn)

The presence of neutral polyamino polyasparagine on the surface gives the nanocapsule stability, long life in the body, protection from the mononuclear phagocyte system and specificity in their interaction with specific target cells.

Presence of Polyasparagine on the surface of the nanocapsules also provides greater specificity toward cancer cells by the systems, since such cells have an increased need of asparagine in order to maintain their development. Cancer cells are unable to self-satisfy their needs of this amino acid, contrary to what happens in normal cells.

As used herein, PAsn includes water soluble salts of PAsn and PAsn water-soluble derivatives.

Nanocapsules comprise an oil and a cationic surfactant in the core.

The oil may be volatile or nonvolatile and in a particular embodiment, is selected from natural, semisynthetic and synthetic oils of pharmaceutical use or a combination thereof, such as animal oils, vegetable oils, hydrocarbon or silicone oils. Suitable oils include, but are not limited to, mineral oil, squalene oil, flavor oils, silicone oil, essential oils, water insoluble vitamins, isopropyl stearate, butyl stearate, octyl palmitate, cetyl palmitate, tridecyl behenate, diisopropyl adipate, dioctyl sebacate, menthyl anthranilate, cetyl octanoate, octyl salicylate, isopropyl myristate, neopentyl glycol dicarpate cetols, Ceraphyls®, decyl oleate, $C_{12}$-$C_{15}$ alkyl lactates, cetyl lactate, lauryl lactate, isostearyl neopentanoate, Myristyl lactate, Isocetyl stearoyl stearate, Octyldodecyl stearoyl stearate, hydrocarbon oils, isoparaffin, fluid paraffins, isododecane, petrolatum, argan oil, canola oil, chile oil, coconut oil, corn oil, cottonseed oil, flaxseed oil, grape seed oil, mustard oil, olive oil, palm oil, palm kernel oil, peanut oil, castor oil, pine seed oil, poppy seed oil, pumpkin seed oil, rice bran oil, Safflower oil, Carthamus, Tea oil, Truffle oil, Vegetable oil, Apricot (kernel) oil, Jojoba oil, Macadamia oil, Wheat germ oil, Almond oil, Soybean oil, Sesame oil, Hazelnut oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil, rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, ethyl oleate, Miglyol™, Labrafil™, Labrafac™, Peceol™ and Maisine™, synthetic and semi-synthetic derivatives thereof, and combinations thereof.

In a more particular embodiment, the oil is chosen from peanut, cottonseed, olive, castor, soybean, safflower, and palm oil; vitamin E, isopropyl myristate, squalane, Miglyol™, Labrafil™, Labrafac™, Peceol™ and Maisine™ or mixtures thereof. Preferred form the oil is Miglyol™.

In the present invention, the term "cationic surfactant" refers to a component having structures and/or functional groups that allow them to interact simultaneously with the lipophilic and hydrophilic portion of the formulation interacting with the latter being favored by the presence of a cationic functional group. In a particular embodiment, the cationic surfactant is selected from primary, secondary and tertiary highly cationizable and quaternary amines. In a more particular embodiment, the cationic surfactant is selected from oleylamine, stearylamine, benzalkonium chloride, benzethonium chloride, cetylpyridinium chloride, cetyltiridinium bromide, dodecyltrimethylammonium bromide, trimethyltetradecylamonium bromide, hexadecyltrimethylammonium bromide and poloxamines (egTetronic™) or mixtures thereof. The cationic surfactant is preferably benzalkonium chloride or hexadecyltrimethylammonium bromide.

Furthermore, the nanocapsules according to the present invention optionally may contain an oil-soluble surfactant, a water-soluble surfactant, or one soluble in both, which sterically favor the system's stability and that allow modulation of the surface charge of the nanocapsules and to provide stability to the system.

In the present invention, the terms "oil-soluble surfactant" or "water-soluble surfactant" refer to components that have structures and/or functional groups that allow them to interact simultaneously with the lipophilic and hydrophilic parts of the formulation, the favored interaction being with the lipophilic part in the case of oil-soluble surfactants or with respect to the hydrophilic part in the case of water-soluble surfactants.

Regarding these optional surfactants, depending on their water/oil solubility, suitable surfactants in the present invention include phospholipids such as lecithin, phosphatidylglycerol, phosphatidylserine, phosphatidylinositol, diphosphatidylglycerol, phosphatidic acid, phosphatidylcholine and phosphatidylethanolamine, cholesterol, glyceryl monostearate, polyoxyethylene polypropylene copolymers (poloxamers), polyethylene glycol, polypropylene glycol, cetyl alcohol, cetostearyl alcohol, stearyl alcohol, alkyl aryl polyether alcohols, fatty acid esters of sorbitan (such as Span™ and Arlacel™), fatty acid esters of polyoxyethylene (as Myrj™) fatty acid esters of polyoxyethylenesorbitan (polysorbate), polyoxyethylenealkyl ethers (macrogol ethers), fatty alcohol ethers (such as Brij™), and mixtures thereof.

According to a preferred embodiment, the oil soluble surfactant is a phospholipid selected from lecithin, phosphatidylglycerol, phosphatidylserine, phosphatidylinositol, diphosphatidylglycerol, phosphatidic acid, phosphatidylcholine and phosphatidylethanolamine, preferably lecithin.

According to another preferred embodiment, the water soluble surfactant is a hydrophilic derivative of polieoxietileno, preferably poloxamer or a polysorbate. In the present invention the term "poloxamer" refers to a nonionic triblock copolymer composed of a central hydrophobic chain of polyoxypropylene connected to two polyoxyethylene hydrophilic chains. A preferred form is poloxamer 188.

As defined above, the nanocapsules of the invention also optionally comprise at least one active ingredient. The term "active ingredient" means any substance used in the treatment, cure, prevention or diagnosis of disease or used to improve the physical and mental health of human beings and animals. The active ingredient may be for example a drug, a vitamin, etc. Nanocapsules systems object of the present invention are suitable for incorporating active ingredients lipophilic or hydrophilic nature. In a preferred embodiment, the active ingredient is docetaxel.

The proportion of active ingredient incorporated in each case depends on the active ingredient to be incorporated, the indication for which it is used and its administration efficiency.

Nanocapsules comprising an oil, a cationic surfactant, a polymer selected from PGA and PGA-PEG and an active ingredient selected from a didemnin or tamandarin fall outside the present patent application and are the subject of European patent application EP11382003.9 with the title "Nanocapsules for use in pharmaceutical compositions," filed on the same day as the present application. Tamandarins didemnins are cyclodepsipeptides and that exhibit a wide variety of biological activities such as antitumor, antiviral and immunosuppressant. Examples of such compounds (excluded from the present invention in nanocapsules of PGA or PGA-PEG) fall within the following general formula:

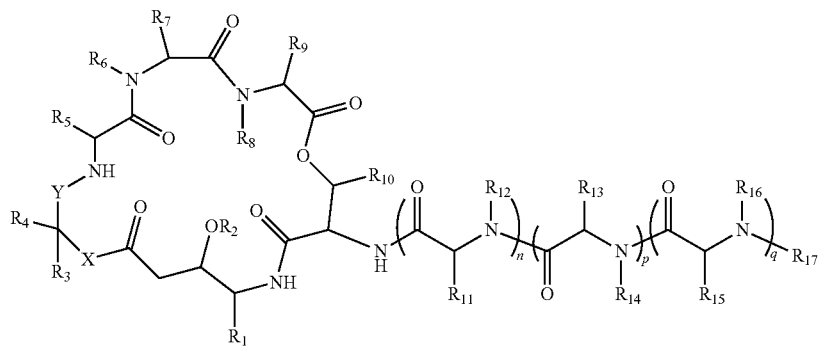

wherein X is selected from O and NH; Y is selected from CO and —COCH (CH3)CO—;

n and p are independently selected from 0 and 1, and q is selected from 0, 1 and 2;

R1, R3, R5, R9, R11, and R15 are independently selected from hydrogen, C1-C6 substituted or unsubstituted alkyl, C2-C6 substituted or unsubstituted alkenyl, and C2-C6 substituted or unsubstituted alkynyl;

R2 is selected from hydrogen, CORa, COORa, C1-C6 substituted or unsubstituted alkyl, C2-C6 substituted or unsubstituted alkenyl, and C2-C6 substituted or unsubstituted alkynyl;

R4, R8, R10, R12, and R16 are independently selected from hydrogen and C1-C6 substituted or unsubstituted alkyl;

R7 and R13 are independently selected from hydrogen, C1-C6 substituted or unsubstituted alkyl, C2-C6 substituted or unsubstituted alkenyl, and C2-C6 substituted or unsubstituted alkynyl; R6 and R14 are independently selected from hydrogen and C1-C6 substituted or unsubstituted alkyl, or R6 and R7 and/or R13 and R14, together with the corresponding N atom and C to which they are attached may form a substituted or unsubstituted heterocyclic group;

R17 is selected from hydrogen, CORa, COORa, CONHRb, COSRc, (C=NRb)ORa, (C=NRb) NHRb, (C=NRb)SRc, (C=S)ORa, (C=5) NHRb, (C=S) SRc, SO2Rc, SO3Rc, C1-C12 substituted or unsubstituted alkyl, C2-C12 substituted or unsubstituted alkenyl, C2-C12 substituted or unsubstituted alkynyl, substituted or unsubstituted aryl, and substituted or unsubstituted heterocyclic group, and Ra, Rb, and Rc are independently selected from hydrogen, C1-C12 substituted or unsubstituted alkyl, C2-C12 substituted or unsubstituted alkenyl, and C2-C12 substituted or unsubstituted alkynyl, substituted or unsubstituted aryl, and substituted heterocyclic group or unsubstituted;

or a pharmaceutically acceptable salt, prodrug or stereoisomer thereof.

In particular, according to the present invention if the nanocapsules comprise polyglutamic acid or polyglutamic-polyethyleneglycol acid (PEG-PGA), then the active ingredient is aplidine.

Manufacturing Procedure

The procedures for obtaining nanocapsule systems are simple methods that avoid drastic conditions such as high temperatures. It is neither necessary to carry out any chemical reaction for obtaining the same, since as indicated previously obtaining this systems involves non-covalent interactions. It thus preserves the integrity of the molecules incorporated into the system, and which may be susceptible of degradation. To achieve the formation of nanocapsules in the desired size range, oily cores are formed comprising an oil and a cationic surfactant, in which surface the coating polymer binds through different types of interaction. It is therefore a solvent diffusion process, which occurs in a controlled manner and provides stability to the system, without the need of creating covalent bonds between the components.

One particular method for preparing the systems of the invention (referred to in the examples solvent diffusion process in stage), comprises:
  a) preparing an aqueous solution comprising a polymer selected from the group consisting of polyglutamic acid (PGA), polyglutamic-polyethyleneglycol acid (PGA-PEG), hyaluronic acid (HA) and polyasparagine (PAsn) or a combination thereof, and optionally a water-soluble surfactant;
  b) preparing an organic solution comprising an oil and a cationic surfactant, and optionally an oil-soluble surfactant;
  c) mixing under stirring the solutions prepared in steps a) and b), spontaneously obtaining the nanocapsules, and
  d) optionally, wholly or partially evaporating to constant volume the organic solvents from the mixture obtained in the previous stage.

In a preferred embodiment the addition of the organic solvent c) can be performed in aliquots of a volume of between 250 µL and 500 µL at time intervals of between 15 and 25 seconds.

Systems of the present invention can be prepared by an alternative procedure (called in the examples solvent diffusion process in two stages) comprising coating a cationic nanoemulsion with the coating polymer by a process of incubation with an aqueous solution of the polymer. Furthermore, the formation of the nanoemulsion may be aided by ultrasound (in the examples called sonication process) or homogenization (in the examples called homogenization procedure).

In a particular embodiment, the incubation process comprises mixing the cationic nanoemulsion with an aqueous solution of coating polymer.

Said cationic nanoemulsion comprises at least an oil, a cationic surfactant and an aqueous phase. The aqueous phase may contain other surfactants, salts, and other auxiliary agents.

The procedures for preparing said nanoemulsion are known in the art, and may comprise a diffusion process, sonication or homogenization (Prego et al. J. NanoSci. Nanotechnol. (2006) 6:1; Tadros et al. Adv. Colloid Interface Sci (2004) 109:303).

One particular method for producing the cationic nanoemulsion (hereinafter in the examples solvent diffusion method) comprises:
  i) preparing an organic solution comprising an oil, a cationic surfactant and optionally an oil soluble surfactant
  ii) adding the solution obtained in step i) over an aqueous phase optionally containing a water-soluble surfactant and is under stirring, to form a cationic nanoemulsion;
  iii) optionally, wholly or partially evaporating to constant volume the organic solvents.

Another particular method of obtaining the cationic nanoemulsion (referred as sonication process in the examples) comprises:
  i) preparing an organic solution comprising an oil, a cationic surfactant and optionally an oil soluble surfactant;
  ii) adding the solution obtained in step i) over an aqueous phase optionally containing a water-soluble surfactant and sonicate;
  iii) diluting with water the emulsion obtained in step ii);
  iv) optionally, wholly or partially evaporating to constant volume the organic solvents.

Another particular method of obtaining the cationic nanoemulsion (referred to as homogenization process in the examples) comprises:
  i) preparing an organic solution comprising an oil, a cationic surfactant and optionally an oil soluble surfactant;
  ii) adding the solution obtained in step i) over an aqueous phase optionally containing a water-soluble surfactant and homogenizing;
  iii) diluting with water the emulsion obtained in step ii) and homogenizing;
  iv) optionally, wholly or partially evaporating to constant volume the organic solvents.

According to particular embodiments of the above methods, if the active ingredient is lipophilic or amphiphilic, said active ingredient is added to the organic solution of step b) or step i). According to other particular embodiments, if the active ingredient is hydrophilic, said active ingredient is added to the solution of step a) or step ii). Preferably, said hydrophilic active ingredient is added dissolved in an aqueous solution. It is also possible to incorporate said hydrophilic active ingredient by adsorption to the suspension of nanocapsules obtained in step d) or after the incubation process once the nanocapsules are formed.

The formation of the nanocapsules are formed by mixing volumes of the above solutions containing cationic nanoemulsion with aqueous solutions of the coating polymer at different ratios, by varying the ratio of coating polymer.

In a particular embodiment, the ratio of PGA, PGA-PEG and HA is between 0.05 and 12% w/w (weight of coating polymer/formulation weight, dry basis). Preferably, the aqueous solution of coating polymer comprises 0.1-25 mg/ml of said polymer.

In another particular embodiment, the PAsn ratio is between 2.5 and 30% w/w (weight of coating polymer/formulation weight, dry basis). Preferably, the aqueous solution of the coating polymer comprises 1-60 mg/ml of said polymer.

The solvent of the organic solution is preferably a mixture of polar solvents such as ethanol and acetone, which may also include non-polar solvents such as dichloromethane. In this organic phase the oil and the cationic surfactant are incorporated, and optionally the oil-soluble surfactant. In a particular embodiment the active ingredient is also added.

A particular example for obtaining nanocapsules systems of the invention comprising PGA or PGA-PEG following the first method described above comprises:
a) preparing an aqueous solution of 20 ml 0.25% w/v of poloxamer 188 in which is dissolved from 0.1 to 25 mg/ml of poly-glutamic acid or polyglutamic-polyethyleneglycol acid;
b) preparing a lecithin oil phase composed of a solution ethanol/acetone and a cationic surfactant (benzalkonium chloride or bromide hexadecyltrimethylammonium), to which Miglyol™ 812 is added.
c) mixing under stirring the resulting solutions of steps a) and b), spontaneously obtaining the nanocapsules;
d) optionally, evaporating to constant volume the organic solvents from the mixture obtained in the previous stage.

A particular example for obtaining nanocapsules systems of the invention of PAsn following the first procedure described above comprises:
a) preparing an aqueous solution of 10 ml volume in which is dissolved from 0.5 to 25 mg of polyasparagine;
b) preparing a lecithin oil phase composed of a solution ethanol/acetone mixture and a cationic surfactant (benzalkonium chloride and hexadecyltrimethylammonium bromide), to which Miglyol™ 812 is added;
c) mixing under stirring the resulting solutions of steps a) and b), spontaneously obtaining the nanocapsules;
d) optionally, evaporating to constant volume the organic solvents from the mixture obtained in the previous stage.

A particular example for obtaining nanocapsules systems of the invention of HA following the first method described above comprises:
a) preparing an aqueous solution of 20 ml at 0.25% w/v of poloxamer 188 in which i 0.1 to 25 mg of hyaluronic acid are dissolved;
b) preparing a lecithin oil phase composed of a solution ethanol/acetone mixture and a cationic surfactant (benzalkonium chloride and hexadecyltrimethylammonium bromide), which is added Miglyol™ 812;
c) mixing under stirring the resulting solutions of steps a) and b), spontaneously obtaining the nanocapsules;
d) optionally, evaporating to constant volume the organic solvents from the mixture obtained in the previous stage.

The method of making nanocapsule systems may include an additional step of lyophilization, in order to preserve them during their storage so that they retain their original characteristics. For lyophilizing the systems the addition of sugars carrying cryoprotective effect is required. Useful sugars to conduct lyophilization include, for example trehalose, glucose, sucrose, mannitol, maltose, polyvinylpyrrolidone (PVP). In lyophilized form, the nanocapsules can be stored for long periods of time, and be easily regenerated, when necessary, simply by adding an optimum volume of water.

In accordance with this additional stage, the present invention also relates to nanocapsule systems comprising a shell of polyglutamic acid, polyglutamic-polyethyleneglycol acid, polyasparagine or hyaluronic acid in the form of a lyophilize.

Nanocapsules systems described herein have suitable stability both in suspension and in lyophilized form. Furthermore, stability studies suggest that when administered to organisms, human or animal, they do not suffer a rapid process of aggregation or destruction, but remain in the nanocapsular form expected until the target tissue or cell is reached.

Nanocapsules systems of this invention have advantages over other drug delivery and/or administration systems, due to their unique behavior in terms of:

Encapsulation/combination of active ingredients: the system may include one or more active ingredients or adjuvants, hydrophilic or lipophilic, in higher proportions than nanoparticles, micelles, complexes, nanogels.

The release of the active ingredient: the shell has a role in the release rate of the same, allowing a controlled release of the active ingredient depending on application and needs.

Stability in biological fluids: the polymeric shell confers lipid cores great stability, which represents an advantage compared to other micro- and nanoemulsion systems.

Specific interaction with certain biological surfaces: the polymeric shell confers lipid cores the possibility of interacting with mucosal surfaces as well as with epithelia and specific cells.

Thus the invention in one particular embodiment relates to a pharmaceutical composition which comprises the nanocapsule systems above, and optionally one or more pharmaceutically acceptable excipients. In particular, the incorporation of active ingredients in the nanocapsules of the invention results in systems whose characteristics in terms of its composition, properties and morphology, makes them excellent candidates for the therapeutic area. The active ingredient to be incorporated in the systems of the invention is one with suitable pharmacotherapeutic properties according to the therapeutic application for which the formulation is intended. In a particular embodiment, the active ingredient is selected from peptides, proteins, lipidic or lipophilic compounds, saccharide compounds, compounds such as nucleic acids or nucleotides oligonucleotides, polynucleotides or combinations of the aforementioned molecules.

In a preferred embodiment, the lipophilic active ingredient is docetaxel.

In a preferred embodiment, the active ingredient is selected from an oligonucleotide, RNA interference, a DNA plasmid or a polynucleotide, more preferably the active ingredient is a DNA plasmid.

In another preferred embodiment, the active ingredient is of a hydrophobic, hydrophilic or amphiphilic nature. The active ingredients of hydrophobic or amphiphilic nature are preferably added in step b) of the method of preparation of nanocapsules of the invention. The active ingredients of hydrophilic in nature are preferably added in step a) of the process or at a later stage to d) by an incubation process. However, the invention also contemplates other embodiments such as adding in step b) an hydrophilic active ingredient dissolved in a small volume of aqueous phase. Unlike the hydrophobic active ingredients, which are encapsulated within the nanocapsules, the active ingredients of hydrophilic nature may be associated to the surface of the same by adsorption.

As defined above, when the polymer included in the nanocapsules of the invention is polyglutamic acid or poliglutamic acid-poliethylen glycol (PGA-PEG), then the active ingredient is not a didemnin or tamandarin.

Such pharmaceutical compositions may be administered by various routes, such as through the mucosa, topically or parenterally.

The proportion of active ingredient incorporated in the systems can be up to about 50% by weight relative to the total weight, dry basis, of the components of the nanocapsule systems. However, the suitable proportion will depend in each case on the active ingredient to be incorporated, the indication for which it is used and administration efficiency. In a particular embodiment, the ratio of lipophilic agent can be up to about 10% by weight, preferably up to about 5%.

As described above, it is possible that the nanocapsule systems described in the present invention incorporate more than one active ingredient, which may be dissolved in the same solution or separately, this depending on the nature of the molecules to be incorporated, preventing any interaction between them, either chemical or physical.

As defined above, the invention relates to the use of said system in the preparation of a medicament. In a particular embodiment, said use relates to the treatment of cancer.

Next, for a greater understanding of the characteristics and advantages of the present invention, reference is made to a number of explanatory examples which complete the previous description, without the invention being limited in any way to them.

EXAMPLES

The following shows the meaning of abbreviations used throughout the examples

PGA=Poly-L-glutamic acid, the salt of PGA used in the following examples was the sodium salt of molecular weight between 15,000 and 50,000 Da (SIGMA).

PGA-PEG 16000 Da=poly-L-glutamic acid-polyethylene glycol, the salt of PGA-PEG used in the following examples was the sodium salt of molecular weight 16,000 Da, in particular with a pegylation percentage of 6% and a chain size of the PEG of 1,000 Da (Alamanda Polymers USA).

PGA-PEG 22000 Da=poly-L-glutamic acid-polyethylene glycol, the salt of PGA-PEG used in the following examples was the sodium salt of molecular weight 22,000 Da, in particular with a pegylation percentage of 93% and chain size of the PEG of 20,000 Da (Alamanda Polymers USA).

PGA-PEG 35000 Da=poly-L-glutamic acid-polyethylene glycol, the salt of PGA-PEG used in the following examples was the sodium salt of molecular weight 35,000 Da, particularly with a pegylation percentage of 60% and chain size of the PEG of 20,000 Da (Alamanda Polymers USA).

HA=hyaluronic acid, the salt of HA used in the following examples was the sodium hyaluronate of molecular weight between 20,000 and 50,000 Da and 165,000 Da. (Imquiaroma, France).

PAsn=polyasparagine; the polyasparagine used preferably has a molecular weight of 5,000 to 15,000 Da, with approximately 5% of aspartic acid residues (SIGMA).

BKC=benzalkonium chloride (SIGMA).

CTAB=Hexadecyltrimethylammonium bromide (SIGMA).

DCX=Docetaxel (SIGMA).

Nanoemulsion (NE)=This term is used for simplicity in the examples to refer to nanosytems made of lecithin, Miglyol™ 812, a cationic surfactant (benzalkonium chloride or hexadecyltrimethylammonium bromide), optionally poloxamer 188 and which only difference with the nanocapsules is the absence of a coating polymer on the surface of the systems.

Nanocapsules (NCs) PGA=This term is used for simplicity in the examples and figures to refer to nanosystems having nanocapsules which comprise lecithin, Miglyol™ 812, benzalkonium chloride, Poloxamer 188 and PGA.

Nanocapsules (NCs) of PGA-PEG=This term is used for simplicity in the examples and figures to refer to nanosystems which nanocapsules comprise a PGA-PEG copolymer of different molecular weight and different percentage of pegylation, lecithin, Miglyol™ 812, benzalkonium chloride, and poloxamer 188.

Nanocapsules (NCs) HA=This term is used for simplicity in the examples and figures to refer to nanosystems which nanocapsules comprise lecithin, Miglyol™ 812, a cationic surfactant (benzalkonium chloride or hexadecyltrimethylammonium bromide), poloxamer 188 and HA.

Nanocapsules (NCs) of PAsn=This term is used for simplicity in the examples and figures to refer to nanosystems which nanocapsules comprise polyasparagine, lecithin, Miglyol™ 812, a cationic surfactant (benzalkonium chloride or hexadecyltrimethylammonium bromide) and optionally poloxamer 188.

Example 1

Evaluation of physical-chemical characteristics of the nanocapsules of PGA and PGA-PEG nanocapsules as a function of polymer amount.

Example 1.1

Nanocapsules were prepared consisting of an oily core coated with PGA or PGA-PEG following the solvent diffusion process in two stages process:
i) An oil phase solution consisting of ethanol/acetone (0.5:9 ml), lecithin (30 mg) and the cationic surfactant benzalkonium chloride (7 mg) was prepared, to which is added 125 μl of Miglyol™ 812.
ii) the solution obtained in step i) is added to about 20 ml of an aqueous solution 0.25% w/v of poloxamer 188 maintained under magnetic stirring for 10 minutes, thus obtained the cationic nanoemulsion spontaneously;
iii) the organic solvents were evaporated to constant volume;
iv) the cationic nanoemulsion obtained in step iii) was coated by an incubation process with an aqueous solution (1.5 ml) comprising 0.1 to 25 mg/ml of polyglutamic-polyethyleneglycol acid or polyglutamic acid of different molecular weights in a ratio 4:1.5 v/v (nanoemulsion:polymer solution), the coating being produced immediately, regardless of the temperature.

Once prepared, their mean diameter is measured, polydispersity index (PI) as well as their surface electric charge (zeta potential). Tables 1, 2, 3, 4 show the values obtained from the above parameters depending on the amount of polyglutamic acid and polyglutamic-polyethyleneglycol acid of different molecular weights in step iv).

TABLE 1

| Formulation | PGA step iv (mg) | Size (nm) | PI | Zeta Potential (mV) |
|---|---|---|---|---|
| NC PGA | 100 | | X | |
| NC PGA | 50 | | X | |
| NC PGA | 25 | | X | |
| NC PGA | 10 | 199 ± 7 | 0.1 | −60 ± 1 |
| NC PGA | 5 | 196 ± 6 | 0.1 | −54 ± 4 |
| NC PGA | 1 | 206 ± 6 | 0.1 | −28 ± 3 |

X = do not form the nanocapsules

TABLE 2

| Formulation | PGA-PEG 16000 Da step iv (mg) | Size (nm) | PI | Zeta Potential (mV) |
|---|---|---|---|---|
| NC PGA-PEG 16000 Da | 100 | | X | |
| NC PGA-PEG 16000 Da | 50 | | X | |
| NC PGA-PEG 16000 Da | 25 | 198 ± 4 | 0.1 | −60 ± 1 |
| NC PGA-PEG 16000 Da | 10 | 194 ± 8 | 0.1 | −55 ± 2 |
| NC PGA-PEG 16000 Da | 5 | 219 ± 15 | 0.2 | −56 ± 1 |
| NC PGA-PEG 16000 Da | 1 | 252 ± 6 | 0.2 | −28 ± 6 |

X = do not form the nanocapsules

TABLE 3

| Formulation | PGA-PEG 22000 Da step iv (mg) | Size (nm) | PI | Zeta Potential (mV) |
|---|---|---|---|---|
| NC PGA-PEG 22000 Da | 100 | 227 ± 6 | 0.1 | −6 ± 1 |
| NC PGA-PEG 22000 Da | 50 | 223 ± 1 | 0.1 | −1 ± 2 |
| NC PGA-PEG 22000 Da | 25 | 225 ± 9 | 0.1 | +2 ± 3 |
| NC PGA-PEG 22000 Da | 10 | 224 ± 2 | 0.1 | +11 ± 2 |
| NC PGA-PEG 22000 Da | 5 | 222 ± 1 | 0.1 | +15 ± 4 |
| NC PGA-PEG 22000 Da | 1 | 211 ± 3 | 0.1 | +26 ± 1 |

TABLE 4

| Formulation | PGA-PEG 35000 Da step iv (mg) | Size (nm) | PI | Zeta Potential (mV) |
|---|---|---|---|---|
| NC PGA-PEG 35000 Da | 100 | 201 ± 10 | 0.1 | −41 ± 1 |
| NC PGA-PEG 35000 Da | 50 | 200 ± 8 | 0.1 | −45 ± 2 |
| NC PGA-PEG 35000 Da | 25 | 210 ± 12 | 0.2 | −29 ± 1 |
| NC PGA-PEG 35000 Da | 10 | 204 ± 3 | 0.1 | −29 ± 2 |
| NC PGA-PEG 35000 Da | 5 | 207 ± 7 | 0.1 | −30 ± 12 |
| NC PGA-PEG 35000 Da | 1 | 263 ± 5 | 0.1 | +2 ± 1 |

Example 1.2

Nanocapsules were prepared consisting of an oily core or PGA or PGA-PEG according to the process of diffusion of the solvent in one stage:
  a) An aqueous solution (20 ml) was prepared wherein from 0.5 to 25 mg/ml of PGA or PGA-PEG at 10 to 0.25% w/v of poloxamer 188 was dissolved;
  b) An oil phase solution was prepared consisting of ethanol/acetone (0.5:9 ml), lecithin (30 mg) and the cationic surfactant benzalkonium chloride (7 mg) to which 125 µl of Miglyol™ 812 were added;
  c) solutions resulting from steps a) and b) were mixed with magnetic stirring for 10 minutes, spontaneously obtaining the nanocapsules;
  d) the organic solvents were evaporated to constant volume.

Once prepared, their mean diameter is measured, polydispersity index and its surface electric charge (zeta potential). Tables 5, 6, 7 and 8 show the values obtained from the above parameters depending on the amount of PGA or PGA-PEG in the aqueous solution of step a).

TABLE 5

| Formulation | PGA step a (mg) | Size (nm) | PI | Zeta Potential (mV) |
|---|---|---|---|---|
| NC PGA | 100 | 170 ± 14 | 0.1 | −57 ± 52 |
| NC PGA | 50 | 155 ± 7 | 0.1 | −57 ± 3 |
| NC PGA | 25 | 178 ± 5 | 0.0 | −43 ± 2 |
| NC PGA | 10 | 202 ± 5 | 0.126 | −45 ± 1.5 |
| NC PGA | 5 | 193 ± 25 | 0.1 | −48 ± 1 |
| NC PGA | 1 | 217 ± 3 | 0.1 | −25 ± 2 |

TABLE 6

| Formulation | PGA-PEG 16000 Da step a (mg) | Size (nm) | PI | Zeta Potential (mV) |
|---|---|---|---|---|
| NC PGA-PEG 16000 Da | 100 | 151 ± 5 | 0.1 | −64 ± 1 |
| NC PGA-PEG 16000 Da | 50 | 172 ± 8 | 0.2 | −67 ± 3 |
| NC PGA-PEG 16000 Da | 25 | 169 ± 4 | 0.1 | −60 ± 1 |
| NC PGA-PEG 16000 Da | 10 | 152 ± 3 | 0.1 | −49 ± 1 |
| NC PGA-PEG 16000 Da | 5 | 166 ± 4 | 0.1 | −42 ± 3 |
| NC PGA-PEG 16000 Da | 1 | 176 ± 5 | 0.1 | −36 ± 2 |

TABLE 7

| Formulation | PGA-PEG 22000 Da step a (mg) | Size (nm) | PI | Zeta Potential (mV) |
|---|---|---|---|---|
| NC PGA-PEG 22000 Da | 100 | 227 ± 1 | 0.1 | −0.5 ± 1 |
| NC PGA-PEG 22000 Da | 50 | 242 ± 1 | 0.1 | +3 ± 4 |
| NC PGA-PEG 22000 Da | 25 | 235 ± 6 | 0.1 | +13 ± 2 |
| NC PGA-PEG 22000 Da | 10 | 222 ± 5 | 0.1 | +16 ± 2 |
| NC PGA-PEG 22000 Da | 5 | 215 ± 1 | 0.1 | +25 ± 1 |
| NC PGA-PEG 22000 Da | 1 | 221 ± 2 | 0.1 | +21 ± 5 |

TABLE 8

| Formulation | PGA-PEG 35000 Da step a (mg) | Size (nm) | PI | Zeta Potential (mV) |
|---|---|---|---|---|
| NC PGA-PEG 35000 Da | 100 | 174 ± 4 | 0.1 | −42 ± 3 |
| NC PGA-PEG 35000 Da | 50 | 188 ± 6 | 0.1 | −39 ± 3 |
| NC PGA-PEG 35000 Da | 25 | 178 ± 5 | 0.1 | −43 ± 1 |
| NC PGA-PEG 35000 Da | 10 | 170 ± 2 | 0.1 | −26 ± 2 |
| NC PGA-PEG 35000 Da | 5 | 192 ± 2 | 0.1 | −15 ± 1 |
| NC PGA-PEG 35000 Da | 1 | 170 ± 4 | 0.1 | −18 ± 2 |

Example 1.3

Nanocapsules were prepared consisting of an oily core and a PGA or PGA-PEG shell following the sonication procedure:
  i) An oil phase composed of a solution of lecithin (30 mg) and the cationic surfactant benzalkonium chloride (7 mg) in dichloromethane (1 ml) was prepared, to which is added 125 µl of Miglyol™ 812;
  ii) the solution obtained in step i) was added to about 2 ml of water containing poloxamer 188 0.25% w/v, and sonicated for 1 minute;
  iii) The emulsion obtained was diluted with water (1:10 dilution);
  iv) the organic solvents were evaporated to constant volume to form a cationic nanoemulsion, and
  v) the cationic nanoemulsion obtained in step iv) was coated by a process of incubation with an aqueous solution (1.5 ml) comprising 0.1 to 25 mg/ml of PGA or PGA-PEG at a rate 4:1.5 (nanoemulsion:solution of PGA or PGA-PEG), immediately producing the shell, irrespective of temperature.

Once prepared, their mean diameter is measured, polydispersity index and its surface electric charge (zeta potential). Tables 9, 10, 11 and 12 show the values obtained from the above parameters depending on the amount of PGA or PGA-PEG in the aqueous solution of step v).

TABLE 9

| Formulation | PGA step v (mg) | Size (nm) | PI | Zeta Potenttial (mV) |
|---|---|---|---|---|
| NC PGA | 100 | X | | |
| NC PGA | 50 | X | | |
| NC PGA | 25 | X | | |
| NC PGA | 10 | 195 ± 1 | 0.1 | −62 ± 4 |
| NC PGA | 5 | 192 ± 2 | 0.1 | −64 ± 1 |
| NC PGA | 1 | 194 ± 4 | 0.1 | −27 ± 2 |

X = do not form the nanocapsules

TABLE 10

| Formulation | PGA-PEG 16000 Da step v (mg) | Size (nm) | PI | Zeta Potenttial (mV) |
|---|---|---|---|---|
| NC PGA-PEG 16000 Da | 100 | X | | |
| NC PGA-PEG 16000 Da | 50 | X | | |
| NC PGA-PEG 16000 Da | 25 | 202 ± 25 | 0.2 | −60 ± 2 |
| NC PGA-PEG 16000 Da | 10 | 194 ± 5 | 0.1 | −57 ± 3 |
| NC PGA-PEG 16000 Da | 5 | 193 ± 4 | 0.1 | −59 ± 2 |
| NC PGA-PEG 16000 Da | 1 | 243 ± 15 | 0.1 | −22 ± 7 |

X = do not form the nanocapsules

TABLE 11

| Formulation | PGA-PEG 22000 Da step v (mg) | Size (nm) | PI | Zeta Potenttial (mV) |
|---|---|---|---|---|
| NC PGA-PEG 22000 Da | 100 | 195 ± 5 | 0.1 | −6 ± 1 |
| NC PGA-PEG 22000 Da | 50 | 180 ± 12 | 0.1 | −4 ± 1 |
| NC PGA-PEG 22000 Da | 25 | 175 ± 9 | 0.1 | −1 ± 1 |
| NC PGA-PEG 22000 Da | 10 | 174 ± 11 | 0.1 | +6 ± 1 |
| NC PGA-PEG 22000 Da | 5 | 172 ± 12 | 0.1 | +10 ± 1 |
| NC PGA-PEG 22000 Da | 1 | 132 ± 10 | 0.3 | +25 ± 1 |

TABLE 12

| Formulation | PGA-PEG 35000 Da step v (mg) | Size (nm) | PI | Zeta Potenttial (mV) |
|---|---|---|---|---|
| NC PGA-PEG 35000 Da | 100 | 203 ± 10 | 0.1 | −45 ± 1 |
| NC PGA-PEG 35000 Da | 50 | 205 ± 1 | 0.1 | −41 ± 1 |
| NC PGA-PEG 35000 Da | 25 | 206 ± 3 | 0.1 | −40 ± 1 |
| NC PGA-PEG 35000 Da | 10 | 209 ± 4 | 0.2 | −31 ± 4 |
| NC PGA-PEG 35000 Da | 5 | 200 ± 15 | 0.1 | −2.2± |
| NC PGA-PEG 35000 Da | 1 | 224 ± 3 | 0.1 | +1 ± 1 |

Example 1.4

Nanocapsules were prepared consisting of an oily core and a PGA or PGA-PEG shell according to the process of homogenization:
i) An oil phase was prepared comprising a solution of lecithin (30 mg) and the cationic surfactant benzalkonium chloride (7 mg) in dichloromethane (1 ml) to which is added 125 μl of Miglyol™ 812;
ii) adding the solution obtained in step i) over 2 ml of water containing 0.25% w/v of poloxamer 188 and homogenizing at 16,000 rpm for 5 minutes and then at 19,000 rpm for another 5 minutes;
iii) The emulsion obtained was diluted with water (1:10 dilution) and homogenized for 3 minutes at 22,000 rpm;
iv) the organic solvents were evaporated to constant volume to form a cationic nanoemulsion, and
v) the nanoemulsion obtained in step iv) was coated by a process of incubation with an aqueous solution (1.5 ml) comprising 0.1 to 25 mg/ml of sodium PGA or PGA-PEG at a rate 4:1.5 (nanoemulsion:PGA or PGA-PEG solution) immediately producing the coating, regardless of temperature.

Once prepared, their mean diameter is measured, polydispersity index and its surface electric charge (zeta potential). Tables 13, 14, 15 and 16 show the values obtained from the above parameters depending on the amount of PGA or PGA-PEG in the aqueous solution of step v).

TABLE 13

| Formulation | PGA step v (mg) | size (nm) | PI | Zeta Potential (mV) |
|---|---|---|---|---|
| NC PGA | 100 | X | | |
| NC PGA | 50 | X | | |
| NC PGA | 25 | X | | |
| NC PGA | 10 | 187 ± 7 | 0.2 | −65 ± 5 |
| NC PGA | 5 | 184 ± 10 | 0.2 | −55 ± 1 |
| NC PGA | 1 | 234 ± 7 | 0.3 | −22 ± 1 |

X = do not form the nanocapsules

TABLE 14

| Formulation | PGA-PEG 16000 Da step v (mg) | size (nm) | PI | Zeta Potential (mV) |
|---|---|---|---|---|
| NC PGA-PEG 16000 Da | 100 | X | | |
| NC PGA-PEG 16000 Da | 50 | X | | |
| NC PGA-PEG 16000 Da | 25 | 199 ± 17 | 0.2 | −69 ± 1 |
| NC PGA-PEG 16000 Da | 10 | 197 ± 7 | 0.1 | −63 ± 1 |
| NC PGA-PEG 16000 Da | 5 | 202 ± 15 | 0.2 | −54 ± 1 |
| NC PGA-PEG 16000 Da | 1 | 206 ± 8 | 0.5 | −22 ± 1 |

X = do not form the nanocapsules

TABLE 15

| Formulation | PGA-PEG 22000 Da step v (mg) | size (nm) | PI | Zeta Potential (mV) |
|---|---|---|---|---|
| NC PGA-PEG 22000 Da | 100 | 201 ± 2 | 0.1 | −8 ± 1 |
| NC PGA-PEG 22000 Da | 50 | 199 ± 1 | 0.2 | −2 ± 1 |
| NC PGA-PEG 22000 Da | 25 | 202 ± 8 | 0.2 | +4 ± 1 |
| NC PGA-PEG 22000 Da | 10 | 210 ± 11 | 0.3 | +14 ± 1 |
| NC PGA-PEG 22000 Da | 5 | 195 ± 1 | 0.2 | +17 ± 3 |
| NC PGA-PEG 22000 Da | 1 | 201 ± 7 | 0.3 | +35 ± 1 |

TABLE 16

| Formulation | PGA-PEG 35000 Da step v (mg) | size (nm) | PI | Zeta Potential (mV) |
|---|---|---|---|---|
| NC PGA-PEG 35000 Da | 100 | 189 ± 14 | 0.2 | −42 ± 2 |
| NC PGA-PEG 35000 Da | 50 | 186 ± 7 | 0.2 | −33 ± 7 |
| NC PGA-PEG 35000 Da | 25 | 206 ± 20 | 0.2 | −37 ± 1 |
| NC PGA-PEG 35000 Da | 10 | 197 ± 17 | 0.2 | −37 ± 1 |

TABLE 16-continued

| Formulation | PGA-PEG 35000 Da step v (mg) | size (nm) | PI | Zeta Potential (mV) |
|---|---|---|---|---|
| NC PGA-PEG 35000 Da | 5 | 194 ± 1 | 0.2 | −24 ± 2 |
| NC PGA-PEG 35000 Da | 1 | 216 ± 20 | 0.2 | +7 ± 1 |

Example 2

Evaluation of the encapsulation capacity of the lipophilic drug docetaxel within 35,000 Da PGA or PGA-PEG nanocapsules Nanocapsules of 35000 Da PGA or PGA-PEG in the form of a sodium salt, an oily core composed of lecithin, Miglyol™ 812 and the cationic surfactant benzalkonium chloride (7 mg) and poloxamer 188 were prepared. Incorporation of a lipophilic drug was effected, docetaxel being used for the occasion, an antitumor agent which is almost insoluble in water. Procedure corresponds to the procedure previously described in Example 1.1., with a modification, since a small aliquot of a stock solution of the active ingredient in ethanol (1-100 mg/ml) is incorporated into the oily phase. Subsequently the system is rotoevaporated to obtain a constant volume and is incubated with a solution of PGA or PGA-PEG 35000 Da forming the nanocapsules encapsulating docetaxel with weight ratios of docetaxel/nanocapsules PGA or PGA-PEG 35000 Da up to 4%.

After preparing the nanocapsules according to the method of the invention, the encapsulation efficiency was determined (evaluating the free drug by high resolution liquid chromatography with λ=227 nm), obtaining an encapsulation efficiency of 60%. Parameters also measured were mean particle diameter, polydispersity index and zeta potential (Table 17).

TABLE 17

| Formulation | size (nm) | PI | Zeta Potential (mV) |
|---|---|---|---|
| NC PGA | 160 ± 4 | 0.1 | −47 ± 2 |
| NC PGA-PEG 35000 Da | 180 ± 4 | 0.1 | −20 ± 4 |

Example 3

Figure 1B:
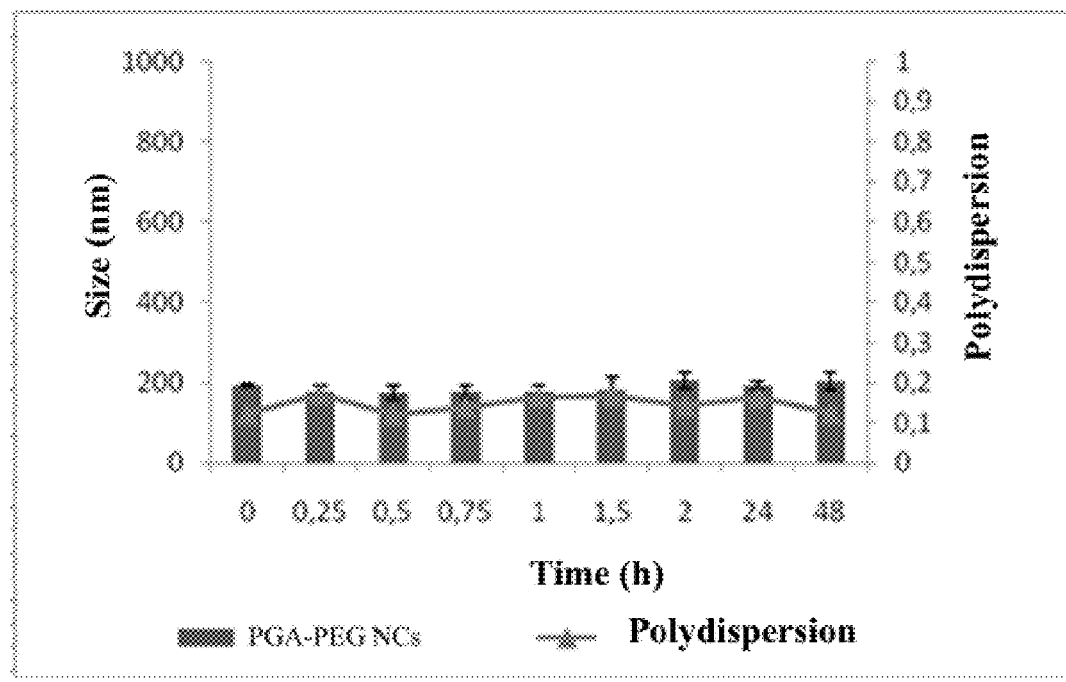

Evaluation of particle size of the formulation of nanocapsules of PGA or PGA-PEG 35000 Da during storage Nanocapsules of 35000 Da PGA or PGA-PEG in the form of a sodium salt, an oily core composed of lecithin, Miglyol™ 812 and the cationic surfactant benzalkonium chloride (7 mg) and poloxamer 188 were prepared according to the previously described method. Measurements were taken for particle size over a relevant time, in order to obtain information on the system's evolution over time. Also, the effect of storage temperature (37° C.) on the stability of nanocapsules was evaluated. The results presented in FIGS. 1a and 1b show the small size variability of the nanocapsules of PGA or PGA-PEG 35000 Da at 5.8% w/w, during storage.

Example 4

Figure 2A:
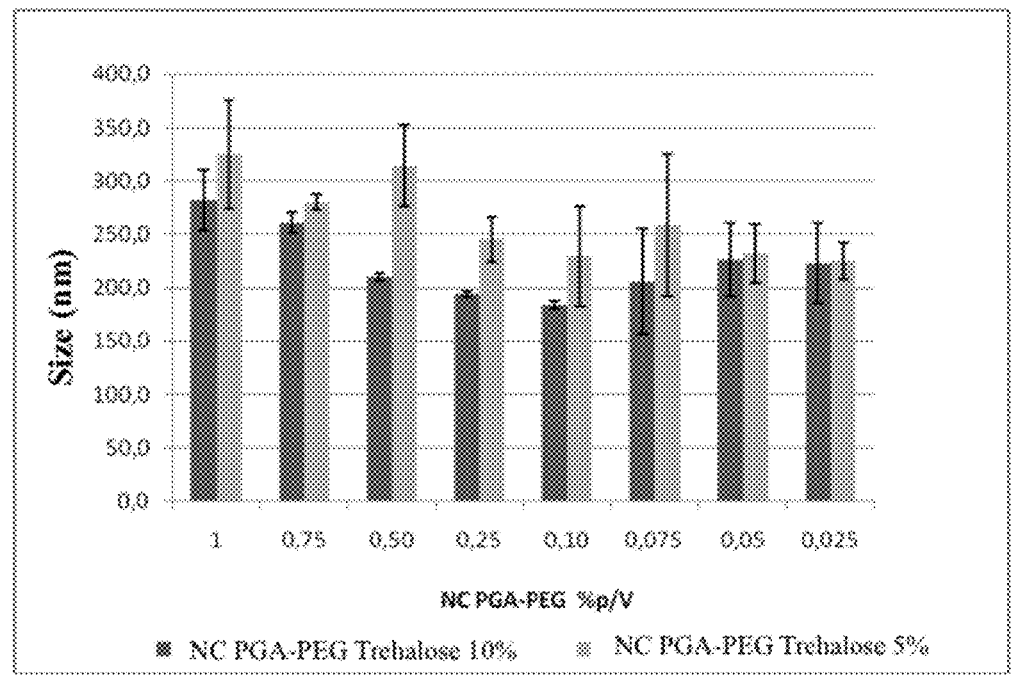
FIG. 2: Particle size polyglutamic-polyethyleneglycol acid nanocapsules (2a) and polyglutamic (2b), after being freeze-dried at various concentrations (0.025 to 1% w/v) with the cryoprotectant trehalose (5 and 10% w/v).
Figure 2B:
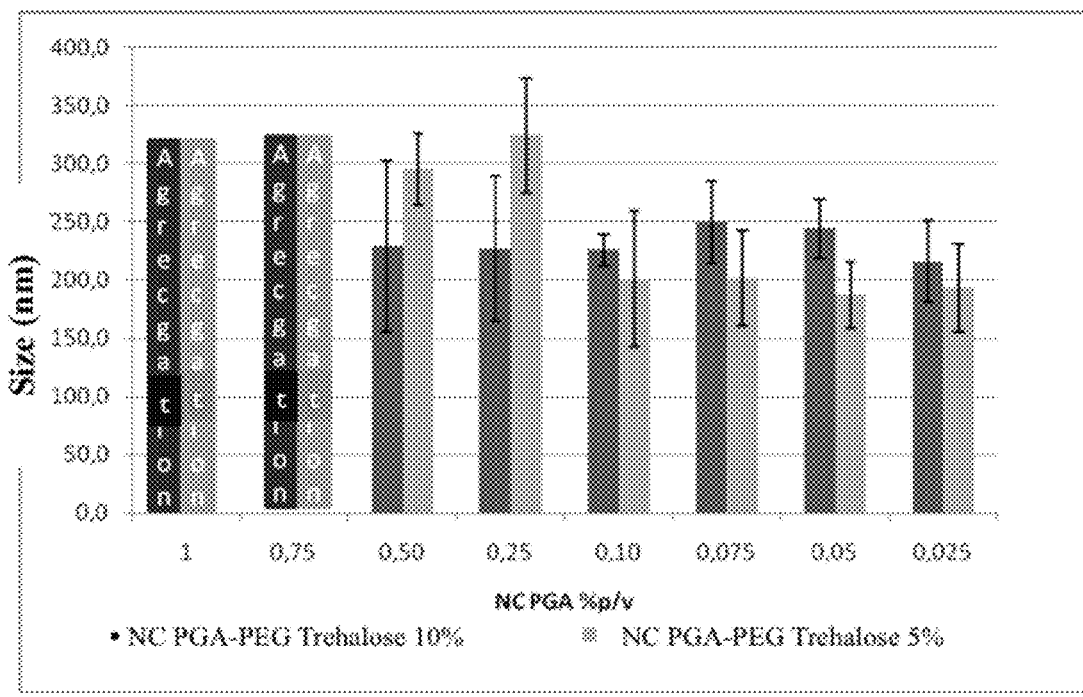

Evaluation of the cryoprotectant effect of trehalose on the particle size of the nanocapsules of PGA or PGA-PEG after the lyophilization process Nanocapsules of 35000 Da PGA or PGA-PEG in the form of a sodium salt, an oily core composed of lecithin, Miglyol™ 812 and the cationic surfactant benzalkonium chloride (7 mg) and poloxamer 188 were prepared according to the previously described method. The cryoprotectant effect of the trehalose was evaluated during lyophilization of PGA or PGA-PEG nanocapsules and the subsequent recovery of particle size after resuspension, by testing two concentrations of trehalose, 5 to 10% w/v. We also evaluated the influence of the concentration of nanocapsules (0.025 to 1% w/v) in the suspension to be lyophilized. The results in FIGS. 2a and 2b show the particle size of the nanocapsules of PGA or PGA-PEG after resuspension.

Example 5

Evaluation of physical-chemical characteristics of the nanocapsules of HA and HA-PEG as a function of polymer amount.

Example 5.1

Nanocapsules were prepared consisting of an oily core coated with HA according to the process of solvent diffusion in two stages:
  i) An oil phase was prepared consisting of a solution of ethanol/acetone (0.5:9 ml), lecithin (30 mg) and cationic surfactants benzalkonium chloride (4 mg) and hexadecyltrimethylammonium bromide (1.8 mg), to which is added 125 μl of Miglyol™ 812.
  ii) adding the solution obtained in step i) over 20 ml of an aqueous solution 0.25% w/v of poloxamer 188 maintained under magnetic stirring for 10 minutes, thus spontaneously obtaining the cationic nanoemulsion;
  iii) evaporating the organic solvents were to constant volume;
  iv) the cationic nanoemulsion obtained in step iii) was coated via an incubation process with an aqueous solution (1.5 ml) comprising 0.1 to 25 mg of sodium hyaluronate in a ratio 4:1.5 nanoemulsion:HA solution) immediately producing the shell, regardless of temperature.

Figure 3:
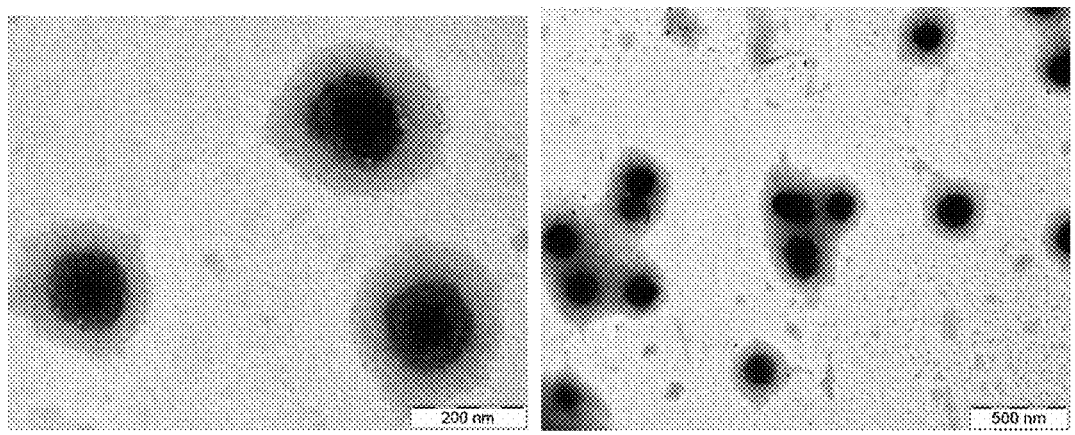
FIG. 3: TEM images of nanocapsules of hyaluronic acid prepared with the cationic surfactant benzalkonium chloride.

Once prepared, their mean diameter is measured, polydispersity index and its surface electric charge (zeta potential) and pictures were taken of the nanocapsules by transmission electron microscopy (FIG. 3). Tables 18 and 19 show the values obtained of the above parameters depending on the amount of HA 20000-50000 Da in step iv) and using benzalkonium chloride or hexadecyltrimethylammonium bromide, respectively. Table 20 shows the values of said parameters depending on the amount of 160000 Da HA added in step iv), and using benzalkonium chloride.

TABLE 18

| Formulation | HA step iv (mg) | size (nm) | PI | Zeta Potential (mV) |
|---|---|---|---|---|
| NE | — | 223 ± 10 | 0.1 | 27 ± 3 |
| NCs HA | 25 | 252 ± 19 | 0.1 | −46 ± 2 |
| NCs HA | 12.5 | 235 ± 13 | 0.1 | −45 ± 4 |
| NCs HA | 6.25 | 248 ± 10 | 0.2 | −42 ± 2 |
| NCs HA | 0.5 | 249 ± 10 | 0.2 | 9 ± 2 |

TABLE 19

| Formulation | HA step iv (mg) | size (nm) | PI | Zeta Potential (mV) |
|---|---|---|---|---|
| NE | — | 215 ± 7 | 0.1 | 35 ± 2 |
| NCs HA | 12.5 | 260 ± 20 | 0.2 | −31 ± 3 |

TABLE 19-continued

| Formulation | HA step iv (mg) | size (nm) | PI | Zeta Potential (mV) |
|---|---|---|---|---|
| NCs HA | 6.25 | 238 ± 3 | 0.1 | −37 ± 2 |
| NCs HA | 3.125 | 238 ± 2 | 0.1 | −35 ± 2 |
| NCs HA | 0.1 | 231 ± 8 | 0.1 | 18 ± 2 |

TABLE 20

| Formulation | HA step iv (mg) | size (nm) | PI | Zeta Potential (mV) |
|---|---|---|---|---|
| NE | — | 207 ± 5 | 0.1 | 27 ± 3 |
| NCs HA | 25 | 410 ± 70 | 0.5 | −59 ± 6 |
| NCs HA | 12.5 | 294 ± 40 | 0.4 | −62 ± 8 |
| NCs HA | 6.25 | 256 ± 11 | 0.5 | −52 ± 8 |
| NCs HA | 1 | 271 ± 53 | 0.5 | 3 ± 1 |
| NCs HA | 0.5 | 235 ± 10 | 0.2 | 27 ± 3 |

Example 5.2

Nanocapsules were prepared consisting of an oily core coated with HA according to the process of solvent diffusion in one step:

a) An aqueous solution is prepared comprising sodium hyaluronate (20 ml) in which is dissolved from 0.5 to 25 mg of HA of 20000-50000 Da and which is at 10 to 0.25% w/v of poloxamer 188;

b) An oily phase was prepared comprising a solution of ethanol/acetone (0.5:9 ml) lecithin (30 mg) and cationic surfactants benzalkonium chloride (4 mg) and hexadecyltrimethylammonium bromide (1.8 mg), to which is added 125 µl of Miglyol™ 812.

c) the resulting solutions of steps a) and b) were mixed with magnetic stirring for 10 minutes, spontaneously obtaining the nanocapsules;

d) the organic solvents were evaporated to constant volume.

Once prepared, their mean diameter is measured, polydispersity index and its surface electric charge (zeta potential). Tables 21 and 22 show the values obtained of the above parameters depending on the amount of HA in step a) and using benzalkonium chloride or hexadecyltrimethylammonium bromide, respectively.

TABLE 21

| Formulation | HA step a (mg) | size (nm) | PI | Zeta Potential (mV) |
|---|---|---|---|---|
| NCs HA | 25 | 186 ± 6 | 0.1 | −47 ± 2 |
| NCs HA | 12.5 | 185 ± 4 | 0.1 | −44 ± 2 |
| NCs HA | 0.5 | 251 ± 5 | 0.1 | 37 ± 1 |

TABLE 22

| Formulation | HA step a (mg) | size (nm) | PI | Zeta Potential (mV) |
|---|---|---|---|---|
| NCs HA | 12.5 | 273 ± 12 | 0.2 | −35 ± 2 |
| NCs HA | 6.25 | 170 ± 6 | 0.1 | −35 ± 1 |
| NCs HA | 3.125 | 168 ± 3 | 0.1 | −35 ± 2 |
| NCs HA | 0.1 | 228 ± 17 | 0.1 | 33 ± 3 |

Example 5.3

Nanocapsules were prepared consisting of an oily core coated with HA according to the sonication process:

i) An oily phase was prepared consisting of a lecithin (30 mg) and the cationic surfactants benzalkonium chloride (4 mg) in dichloromethane, to which is added 125 µl of Miglyol™ 812;

ii) adding the solution obtained in step i) over 2 ml of an aqueous solution 0.25% w/v of poloxamer 188 and sonicating for 1 minute;

iii) The emulsion obtained was diluted with water (1:10 dilution)

iv) evaporating the organic solvents to constant volume to form the cationic nanoemulsion;

v) the cationic nanoemulsion obtained in step iv) was coated via an incubation process with an aqueous solution (1-5 ml) comprising 0.5 to 25 mg of sodium hyaluronate in a ratio 4:1.5 nanoemulsion:HA solution) immediately producing the shell, regardless of temperature.

Once prepared, their mean diameter is measured, polydispersity index and its surface electric charge (zeta potential). Table 23 shows the values obtained of the above parameters depending on the amount of HA in step v).

TABLE 23

| Formulation | HA step v (mg) | size (nm) | PI | Zeta Potential (mV) |
|---|---|---|---|---|
| NE | — | 162 ± 3 | 0.2 | 40 ± 4 |
| NCs HA | 25 | 200 ± 3 | 0.2 | −43 ± 6 |
| NCs HA | 12.5 | 179 ± 5 | 0.1 | −47 ± 2 |
| NCs HA | 6.25 | 185 ± 2 | 0.2 | −43 ± 2 |
| NCs HA | 0.5 | 177 ± 1 | 0.2 | 14 ± 2 |

Example 5.4

Nanocapsules were prepared consisting of an oily core coated with HA by the process of homogenization:

i) an oily phase was prepared comprising a solution of lecithin (30 mg) and the cationic surfactant benzalkonium chloride (4 mg) in dichloromethane (1 ml), to which is added 125 µl of Miglyol™ 812;

ii) the solution obtained in step i) was added over 2 ml of water containing 0.25% w/v of poloxamer 188 and homogenized at 16,000 rpm for 5 minutes and then at 19,000 rpm for another 5 minutes;

iii) The emulsion obtained was diluted with water (1:10 dilution) and homogenized for 3 minutes at 22,000 rpm;

iv) the organic solvents were evaporated to constant volume to form a cationic nanoemulsion, and v) the cationic nanoemulsion obtained in step iv) was coated via an incubation process with an aqueous solution (1.5 ml) comprising 0.5 to 25 mg of sodium hyaluronate in a ratio 4:1.5 nanoemulsion:HA solution) immediately producing the shell, regardless of temperature.

Once prepared, their mean diameter is measured, polydispersity index and its surface electric charge (zeta potential). Table 24 shows the values obtained of the above parameters depending on the amount of HA in step a).

TABLE 24

| Formulation | HA step v (mg) | size (nm) | PI | Zeta Potential (mV) |
|---|---|---|---|---|
| NE | — | 141 ± 9 | 0.3 | 49 ± 1 |
| NCs HA | 25 | 166 ± 18 | 0.2 | −44 ± 2 |
| NCs HA | 12.5 | 143 ± 3 | 0.2 | −42 ± 3 |
| NCs HA | 0.5 | 214 ± 5 | 0.3 | 37 ± 6 |

Example 6

Evaluation of the encapsulation capacity of the lipophilic drug docetaxel in HA nanocapsules Nanocapsules were prepared comprising HA as a sodium salt, an oily core composed of lecithin, Miglyol™ 812 and the cationic surfactants benzalkonium chloride (4 mg) or bromide hexadecyltrimethylammonium (1.8 mg) and poloxamer 188. Incorporation of a lipophilic drug was effected, docetaxel being used for the occasion, an antitumor agent which is almost insoluble in water. Procedure corresponds to the procedure previously described in Example 5.1., with a modification, since a small aliquot of a stock solution of the active ingredient in ethanol (1-100 mg/ml) is incorporated into the oily phase. Subsequently the system is rotoevaporated to obtain a constant volume and is incubated with a solution of HA forming the nanocapsules encapsulating docetaxel with weight ratios of docetaxel/nanocapsules HA up to 4%.

After preparing the nanocapsules according to the method of the invention, the encapsulation efficiency was determined (evaluating the free drug by high resolution liquid chromatography with $\lambda$=227 nm), obtaining an encapsulation efficiency of about 65%. Parameters also measured were mean particle diameter, polydispersity index and zeta potential (Table 25).

TABLE 25

| Formulation | Size (nm) | PI | Zeta Potential (mV) |
|---|---|---|---|
| NC BKC-HA | 235 ± 13 | 0.1 | −45 ± 4 |
| NC BKC-HA/DCX | 250 ± 20 | 0.1 | −52 ± 11 |
| NC CTAB-HA | 267 ± 23 | 0.1 | −31 ± 3 |
| NC CTAB-HA/DCX | 276 ± 1 | 0.1 | −36 ± 1 |

Example 7

Docetaxel drug release from HA nanocapsules

Figure 4:
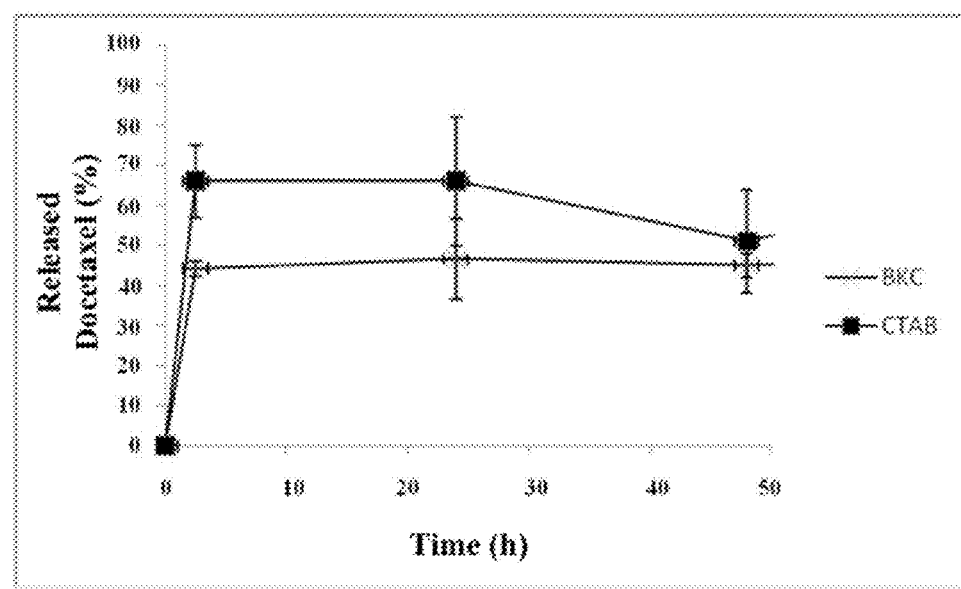
FIG. 4: Release profile of docetaxel (DCX) obtained from hyaluronic acid nanocapsules prepared with the cationic surfactants benzalkonium chloride (BKC) and hexadecyltrimethylammonium bromide (CTAB).

HA nanocapsules were prepared by encapsulating the lipophilic drug docetaxel following the procedure described in Example 6. The nanocapsules were diluted in water and incubated in this medium with horizontal shaking (100 rpm) at 37° C. At different times samples were taken from the incubation media and nanocapsules were isolated in suspension by ultracentrifugation. Finally we evaluated the fraction of drug released quantifying the amount of free drug in infranate liquid which was compared with the fraction of drug remaining bound to the nanocapsules. Docetaxel quantification was performed as described in Example 6. The drug release profile of the nanocapsules of HA is included in FIG. 4.

Example 8

Evaluation of particle size of the HA nanocapsule formulations during storage

Figure 5A:
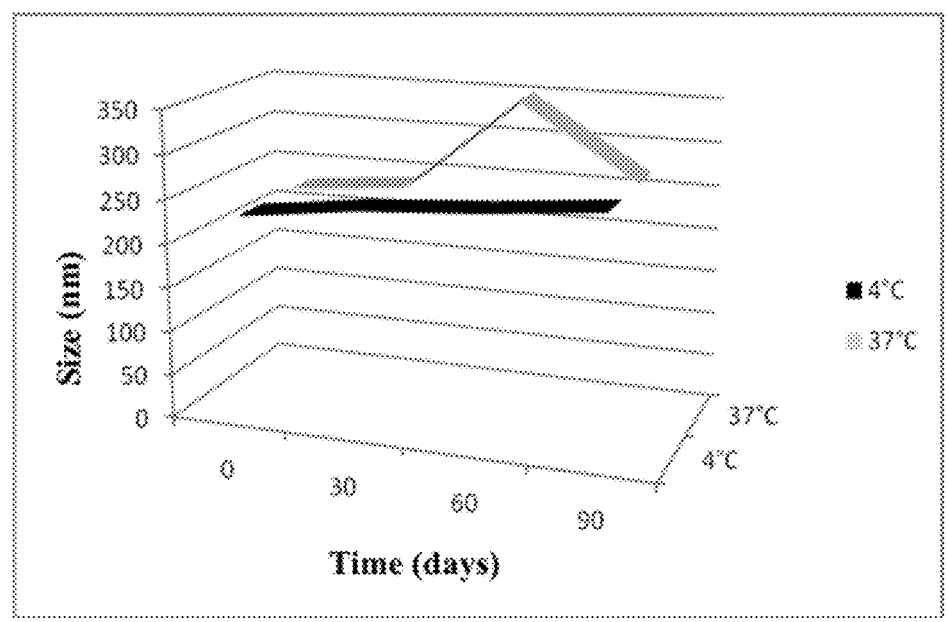
FIG. 5: Particle size evolution of hyaluronic acid nanocapsules prepared with the cationic surfactant benzalkonium chloride (5.a) and hexadecyltrimethylammonium bromide (5.b) in storage at 4° C. and 37° C., for a period 3 months.
Figure 5B:
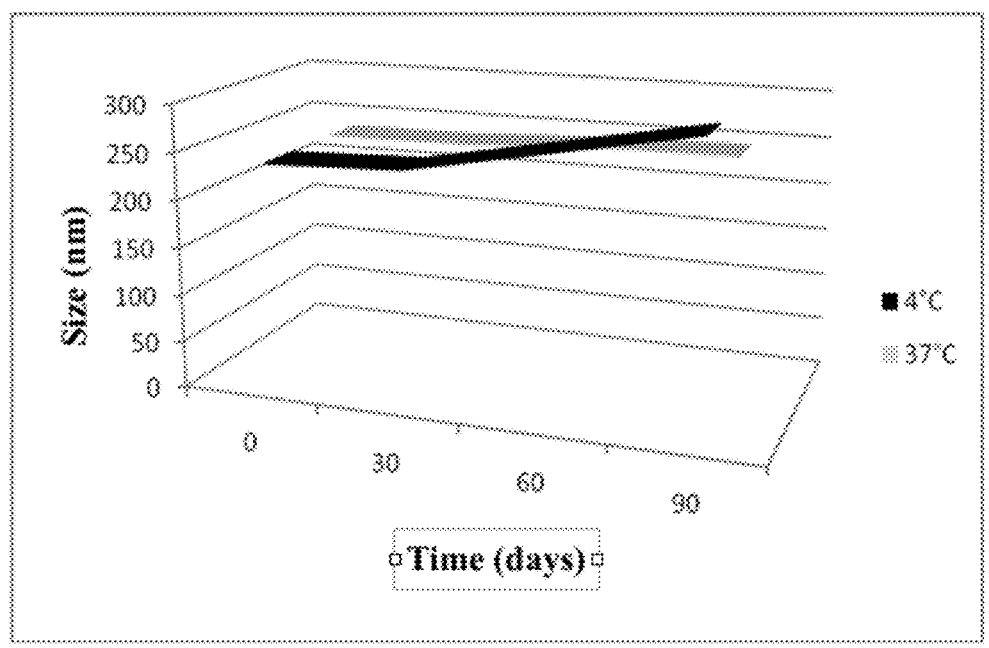

HA nanocapsules were prepared as a sodium salt, having an oily core composed of lecithin, Miglyol™ 812 and the cationic surfactant benzalkonium chloride (7 mg) or hexadecyltrimethylammonium (5.4 mg) and poloxamer 188 according to the previously described method. Measurements were taken for particle size over a relevant time, in order to obtain information on the system's evolution over time. Also, the effect of storage temperature (4 and 37° C.) on the stability of nanocapsules was evaluated. The results presented in FIGS. 5a and 5b show the small size variability of the nanocapsules of HA at 5.8% w/w, with benzalkonium chloride and hexadecyltrimethylammonium bromide, respectively, during storage.

Example 9

Figure 6:
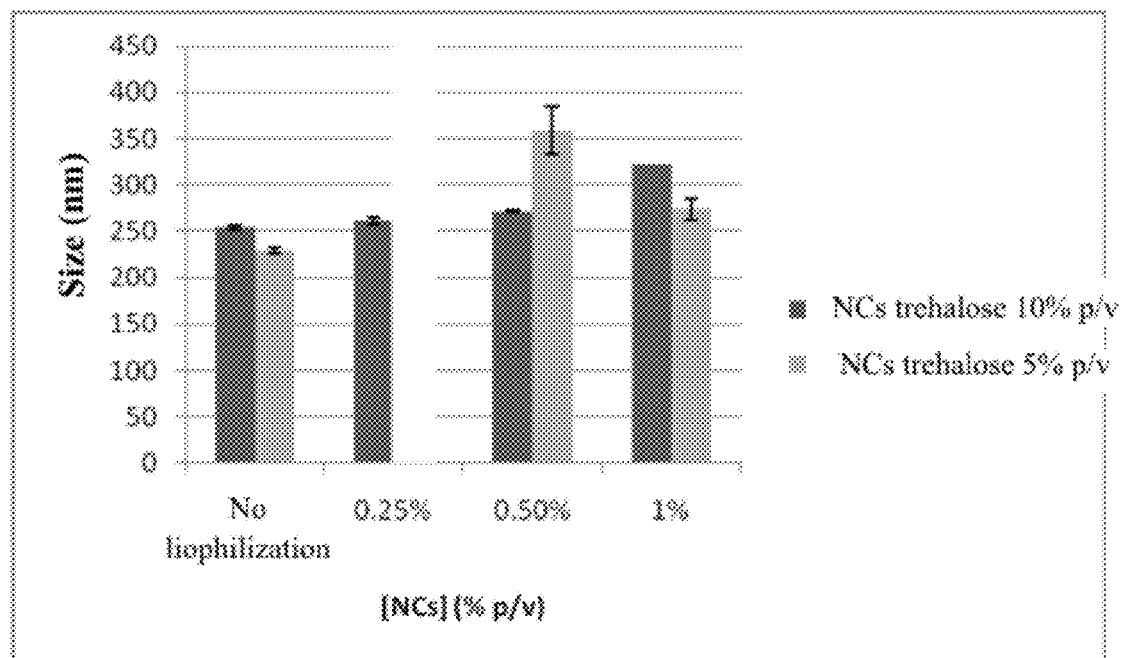
FIG. 6: Particle size of nanocapsules of hyaluronic acid prepared with the cationic surfactant benzalkonium chloride, after being lyophilized at different concentrations (0.25-1% w/v) with the cryoprotectant trehalose (5 and 10% w/v).

Evaluation of the cryoprotectant effect of trehalose on the particle size of the nanocapsules of HA after the lyophilization process Nanocapsules of HA in the form of a sodium salt, an oily core composed of lecithin, Miglyol™ 812 and the cationic surfactant benzalkonium chloride (4 mg) and poloxamer 188 were prepared according to the previously described method. The cryoprotectant effect of the trehalose was evaluated during lyophilization of HA nanocapsules and the subsequent recovery of particle size after resuspension, by testing two concentrations of trehalose, 5 to 10% w/v. We also evaluated the influence of the concentration of nanocapsules (0.25, 0.5 and 1% w/v) in the suspension to be lyophilized. The results in FIG. 6 show the particle size of the nanocapsules of HA after resuspension.

Example 10

Study of the capacity to inhibit cell proliferation of HA nanocapsules

Figure 7A:
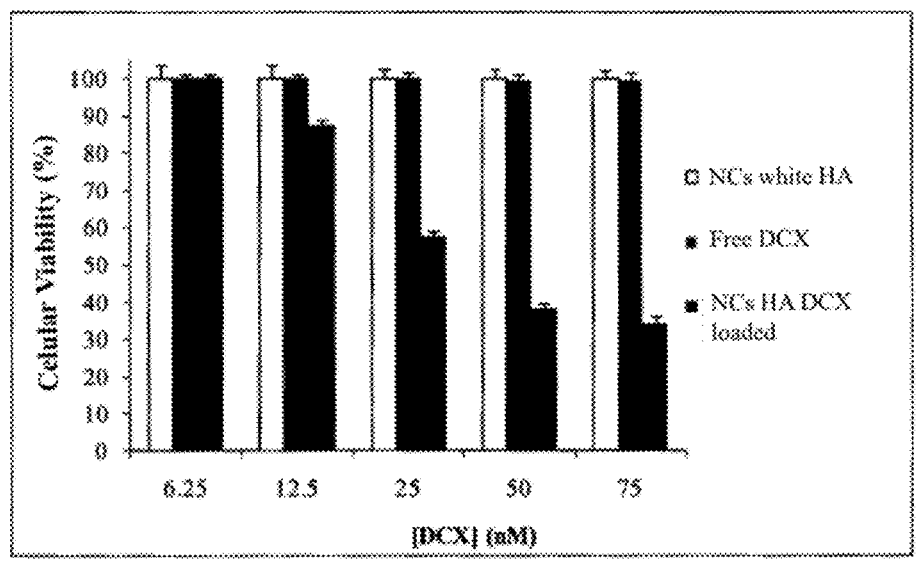
FIG. 7: Viability of cancer cell line NCI-H460 after two (7.a) and 48 (7.b) hours in contact with hyaluronic acid nanocapsules (NCs HA) white, docetaxel (DCX) in solution, and hyaluronic acid nanocapsules containing docetaxel, varying concentrations of the antitumor agent. The cationic surfactant used in the preparation of the nanocapsules was hexadecyltrimethylammonium bromide.
Figure 7B:
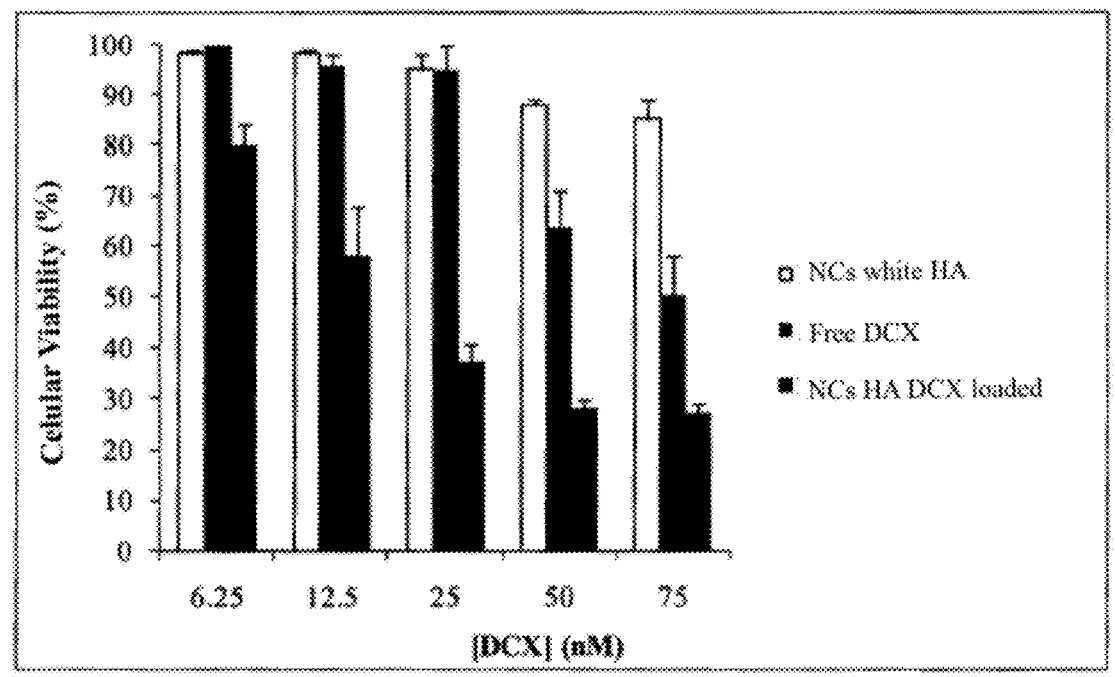

In order to evaluate the potential of HA nanocapsules encapsulating cytostatic docetaxel molecule to inhibit cell proliferation of lung cancer cell line NCI-H460, HA nanocapsules were prepared using hexadecyltrimethylammonium bromide (1.8 mg) according to the procedure described in Example 6. The results in FIG. 7 show the greatest ability to inhibit the proliferation of nanocapsules encapsulating docetaxel compared to the free molecule when systems are brought into contact for 2 to 48 h with the cancer cells. Moreover, one can see the safety of the systems without docetaxel. IC50 values, the concentration which produces 50% mortality of the population, was calculated using Graph Pad Prism 2.1 (Graph Pad Software). Thus, the solution of docetaxel showed IC50 values of 105 nM and 36 nM when in contact with the cells for 2 to 48 respectively, while the formulations of HA nanocapsules encapsulating docetaxel showed values of about 29 and 13 nM in the same Incubation times, the docetaxel nanoencapsulation being 3.6 and 2.8 times more effective at inhibiting cell proliferation.

Example 11

Evaluation of physical-chemical characteristics of PAsn nanocapsules according to the amount of polymer.

Example 11.1

Nanocapsules were prepared consisting of an oily core coated with PAsn according to the process of solvent diffusion in two stages:
i) An oily phase was prepared consisting of a solution of ethanol/acetone (0.5:9 ml), lecithin (30 mg) and cationic surfactants benzalkonium chloride (4 mg) and hexadecyltrimethylammonium bromide (1.8 mg), to which is added 125 µl of Miglyol™ 812.

ii) adding the solution obtained in step i) over 10 ml of water maintained under magnetic stirring for 10 minutes, thus spontaneously obtaining the cationic nanoemulsion;

iii) evaporating the organic solvents were to constant volume;

iv) the cationic nanoemulsion obtained in step iii) was coated via an incubation process with an aqueous solution (1 ml) comprising different amounts of PAsn in a ratio 3.7:1 immediately producing the shell, regardless of temperature.

Figure 8A:
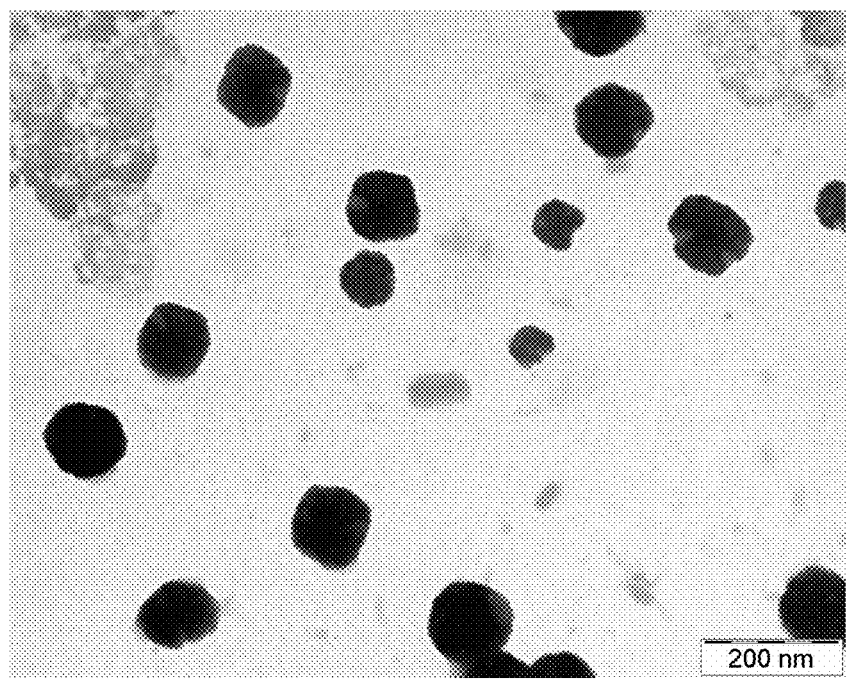
FIG. 8: TEM images of polyasparagine nanocapsules prepared with the cationic surfactant benzalkonium chloride (8.a) or hexadecyltrimethylammonium bromide (8.b).
Figure 8B:
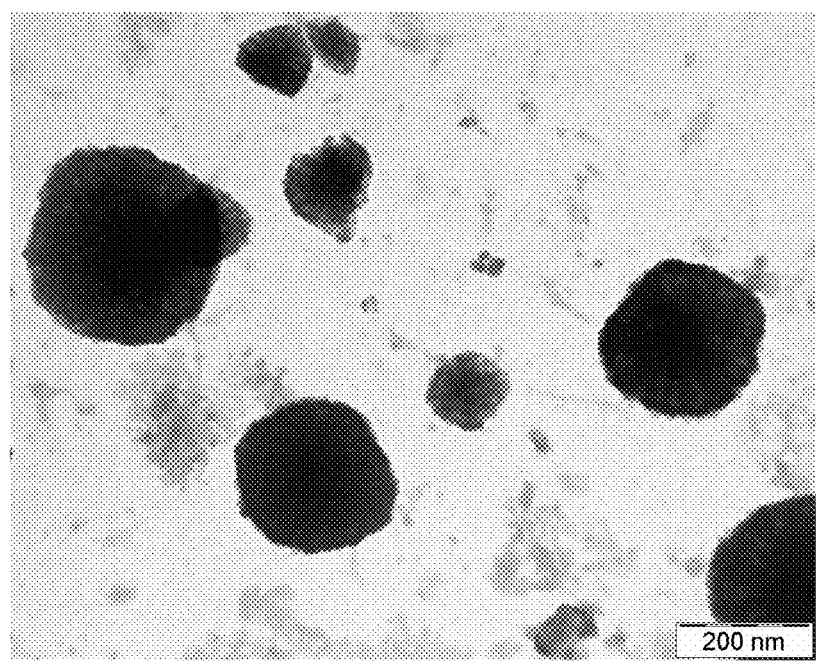

Once prepared, their mean diameter is measured, polydispersity index and its surface electric charge (zeta potential) and pictures were taken of the nanocapsules by transmission electron microscopy (FIG. 8). Tables 26 and 27 show the values obtained of the above parameters depending on the amount of PAsn in step iv) and using benzalkonium chloride or hexadecyltrimethylammonium bromide, respectively.

TABLE 26

| Formulation | PAsn step iv (mg) | Size (nm) | IP | Zeta Potential (mV) |
|---|---|---|---|---|
| NE | — | 215 ± 7 | 0.1 | 34 ± 3 |
| NCs PAsn | 100 | 253 ± 16 | 0.2 | −36 ± 9 |
| NCs PAsn | 50 | 250 ± 13 | 0.1 | −36 ± 6 |
| NCs PAsn | 25 | 243 ± 19 | 0.1 | −39 ± 2 |
| NCs PAsn | 10 | 235 ± 5 | 0.1 | −33 ± 4 |
| NCs PAsn | 5 | 262 ± 3 | 0.1 | −19 ± 2 |
| NCs PAsn | 1 | 370 ± 13 | 0.2 | 10 ± 2 |

TABLE 27

| Formulation | PAsn step iv (mg) | Size (nm) | IP | Zeta Potential (mV) |
|---|---|---|---|---|
| NE | — | 208 ± 10 | 0.1 | 40 ± 3 |
| NCs PAsn | 100 | 270 ± 5 | 0.2 | −15 ± 9 |
| NCs PAsn | 50 | 263 ± 8 | 0.2 | −20 ± 6 |
| NCs PAsn | 25 | 249 ± 19 | 0.2 | −23 ± 2 |
| NCs PAsn | 10 | 214 ± 9 | 0.1 | −24 ± 4 |
| NCs PAsn | 5 | 290 ± 3 | 0.2 | −8 ± 2 |
| NCs PAsn | 1 | 339 ± 16 | 0.2 | 10 ± 2 |

Example 11.2

Nanocapsules were prepared consisting of an oily core coated according PAsn solvent diffusion process in one step
a) polyasparagine aqueous solution (20 ml) was prepared with varying quantities of the polyamino acid, 5-200 mg;
b) An oil phase was prepared composed of a solution ethanol/acetone (0.5:9 ml), lecithin (30 mg) and the cationic surfactant benzalkonium chloride (4 mg) and hexadecyltrimethylammonium bromide (1.8 mg) which is added 125 l of Miglyol™ 812;
c) the resulting solutions of steps a) and b) were mixed with magnetic stirring for 10 minutes, spontaneously obtaining the nanocapsules;
d) the organic solvents were evaporated to constant volume.

Once prepared, their mean diameter is measured, polydispersity index and its surface electric charge (zeta potential). Tables 28 and 29 show the values obtained of the above parameters depending on the amount of PAsn in step a) and using benzalkonium chloride or hexadecyltrimethylammonium bromide, respectively.

TABLE 28

| Formulation | PAsn step a (mg) | Size (nm) | IP | Zeta Potential (mV) |
|---|---|---|---|---|
| NCs PAsn | 10 | — | — | — |
| NCs PAsn | 50 | 323 ± 16 | 0.2 | −23 ± 13 |
| NCs PAsn | 25 | 250 ± 7 | 0.2 | −20 ± 6 |
| NCs PAsn | 10 | 215 ± 9 | 0.1 | −18 ± 1 |
| NCs PAsn | 5 | 196 ± 9 | 0.2 | −6 ± 1 |
| NCs PAsn | 1 | 356 ± 6 | 0.2 | 13 ± 5 |

TABLE 29

| Formulation | PAsn step a (mg) | Size (nm) | IP | Zeta Potential (mV) |
|---|---|---|---|---|
| NCs PAsn | 10 | — | — | — |
| NCs PAsn | 50 | 366 ± 5 | 0.3 | −22 ± 6 |
| NCs PAsn | 25 | 260 ± 4 | 0.2 | −20 ± 7 |
| NCs PAsn | 10 | 173.9 ± 5 | 0.1 | −24 ± 3 |
| NCs PAsn | 5 | 140 ± 3 | 0.2 | −14 ± 2 |
| NCs PAsn | 1 | 332 ± 9 | 0.2 | 13 ± 6 |

Example 11.3

Nanocapsules were prepared consisting of an oily core coated with PAsn according to the sonication process:
i) An oily phase was prepared consisting of a lecithin (30 mg) and the cationic surfactants benzalkonium chloride (4 mg) or CTAB (1.8 mg) in dichloromethane (1 ml), to which is added 200 µl of Miglyol™ 812;
ii) adding the solution obtained in step i) over 2 ml of water and sonicating for 2 minutes;
iii) The emulsion obtained was diluted with water (1:10 dilution)
iv) evaporating the organic solvents to constant volume to form the cationic nanoemulsion;
v) the cationic nanoemulsion obtained in step iv) was coated via an incubation process with an aqueous solution (5 ml) comprising variable amounts of PAsn in a ratio 4:1 (nanoemulsion:PAsn solution) immediately producing the shell, regardless of temperature.

Once prepared, their mean diameter is measured, polydispersity index and its surface electric charge (zeta potential). Table 30 shows the values obtained.

Example 11.4

Nanocapsules were prepared consisting of an oily core coated with polyasparagine by the process of homogenization:
i) an oily phase was prepared comprising a solution of lecithin (30 mg) and the cationic surfactant benzalkonium chloride (4 mg) or CTAB (1.8 mg) in dichloromethane (1 ml), to which is added 125 µl of Miglyol™ 812;
ii) the solution obtained in step i) was added over 2 ml of water and homogenized at 16,000 rpm for 5 minutes and then at 19,000 rpm for another 5 minutes;
iii) The emulsion obtained was diluted with water (1:10 dilution) and homogenized for 3 minutes at 22,000 rpm;

iv) the organic solvents were evaporated to constant volume to form a cationic nanoemulsion, and v) the cationic nanoemulsion obtained in step iv) was coated via an incubation process with an aqueous solution (1 ml) comprising variable amounts of PAsn in a ratio 4:1.5 (nanoemulsion:PAsn solution) immediately producing the shell, regardless of temperature.

Once prepared, their mean diameter is measured, polydispersity index and its surface electric charge (zeta potential). Table 30 shows the values obtained of the above parameters.

TABLE 30

| Method | Surfactant | Amount surfactant (mg) | Amount PAsn | Size (nm) | IP | Zeta Potential (mV) |
|---|---|---|---|---|---|---|
| Sonication | CTAB | 1.8 | 1 mg/mL | 226 ± 5 | 0.1 | −30 ± 4 |
| Sonication | BKC | 4 | 1 mg/mL | 242 ± 3 | 0.2 | −37 ± 5 |
| Homogeneization | CTAB | 1.8 | 1 mg/mL | 236 ± 2 | 0.1 | −31 ± 1 |
| Homogeneization | BKC | 4 | 1 mg/mL | 254 ± 3 | 0.2 | −34 ± 6 |

Example 12

Evaluation of the encapsulation capacity of the lipophilic drug docetaxel nanocapsules polyasparagine Nanocapsules were prepared comprising PAsn, an oily core composed of lecithin, Miglyol™ 812 and the cationic surfactants benzalkonium chloride (4 mg) or bromide hexadecyltrimethylammonium (1.8 mg). Incorporation of a lipophilic drug, docetaxel, an antitumor agent which is almost insoluble in water was effected. Procedure corresponds to the procedure previously described in Example 11.1., with a small modification, a small aliquot of a stock solution of the active ingredient in ethanol (1-100 mg/ml) is incorporated into the oily phase. Subsequently the system is rotoevaporated to obtain a constant volume and is incubated with a solution of PAsn forming the nanocapsules encapsulating docetaxel with weight ratios of docetaxel/nanocapsules PAsn up to 30%.

After preparing the nanocapsules according to the method of the invention, the encapsulation efficiency was determined (evaluating the free drug by high resolution liquid chromatography with $\lambda$=227 nm), obtaining an encapsulation efficiency of about 75%. Parameters also measured were mean particle diameter, polydispersity index and zeta potential (Table 31).

TABLE 31

| Formulation | Size (nm) | PI | Zeta Potential (mV) | % association |
|---|---|---|---|---|
| NC BKC-PAsn | 254 ± 6 | 0.1 | −33 ± 6 | — |
| NC BKC-PAsn DCX | 249 ± 7 | 0.1 | −36 ± 11 | 75 ± 3 |
| NC CTAB-PAsn | 235 ± 7 | 0.1 | −28 ± 3 | — |
| NC CTAB-PAsn DCX | 236 ± 12 | 0.1 | −32 ± 8 | 76 ± 2 |

Example 13

Drug release docetaxel form the polyasparagine nanocapsules

Figure 9:
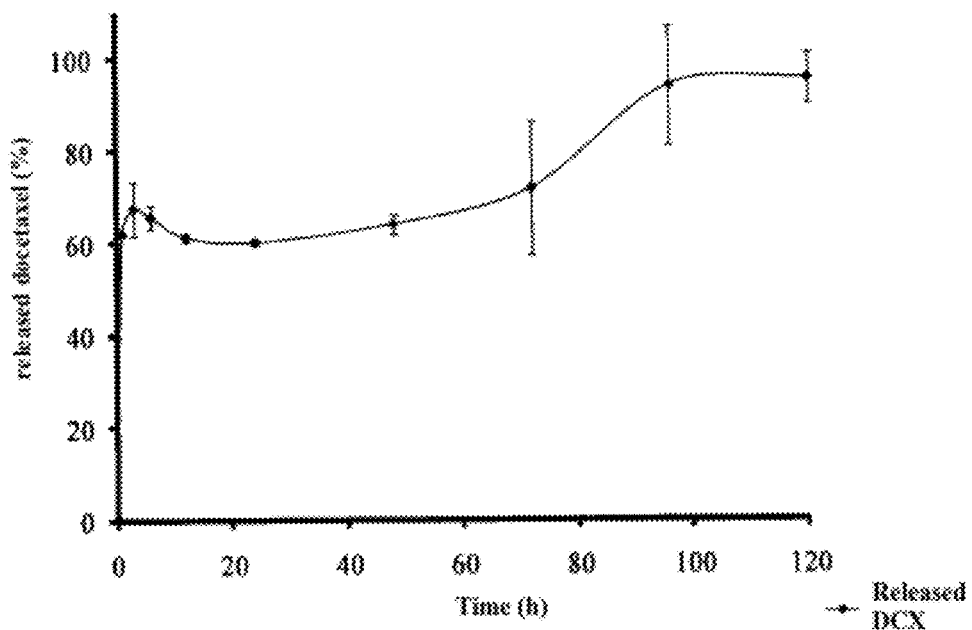
FIG. 9: Release profile of docetaxel (DCX) obtained from polyasparagine nanocapsules prepared with cationic surfactant hexadecyltrimethylammonium bromide.

PAsn nanocapsules were prepared by encapsulating the lipophilic drug docetaxel following the procedure described in Example 12. The nanocapsules were diluted in water and incubated in this medium with horizontal shaking (100 rpm) at 37° C. At different times samples were taken from the incubation media and nanocapsules were isolated in suspension by ultracentrifugation. Finally we indirectly evaluated the fraction of drug released quantifying the amount of drug found in the nanocapsules. Docetaxel quantification was performed as described in Example 12. The drug release profile of the nanocapsules of PAsn is included in FIG. 9.

Example 14

Figure 10A:
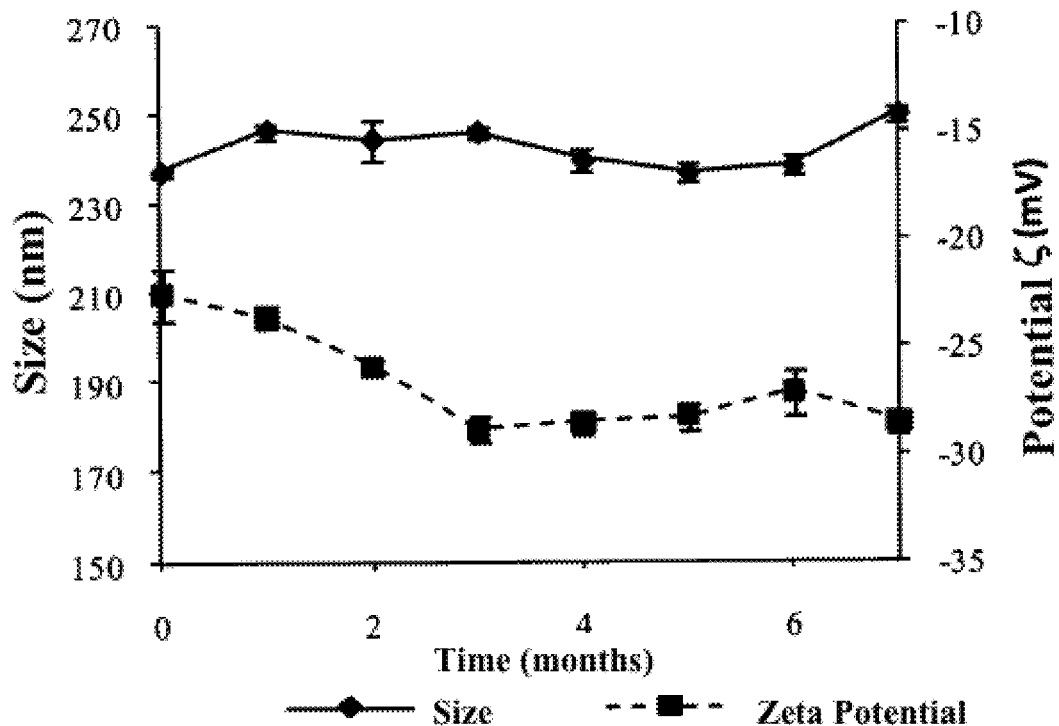
FIG. 10: Evolution of particle size and zeta potential of polyasparagine nanocapsules prepared with the cationic surfactant hexadecyltrimethylammonium bromide during storage at 4° C. (10.a) and 37° C. (10.b) and the same systems prepared with the cationic surfactant benzalkonium chloride during storage at 4° C. (10.c) and 37° C. (10.d).
Figure 10B:
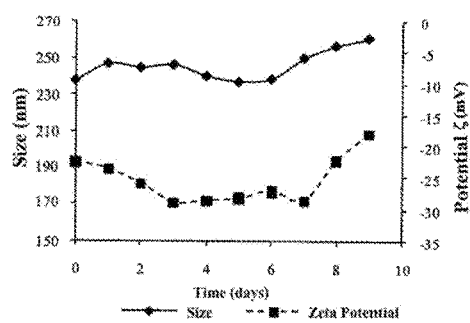
Figure 10C:
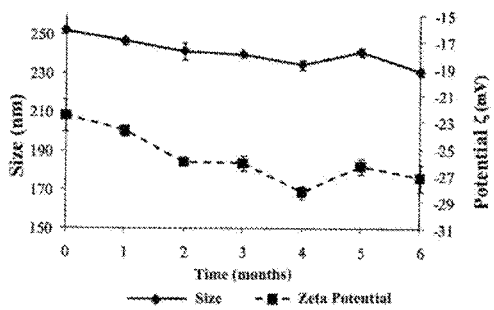
Figure 10D:
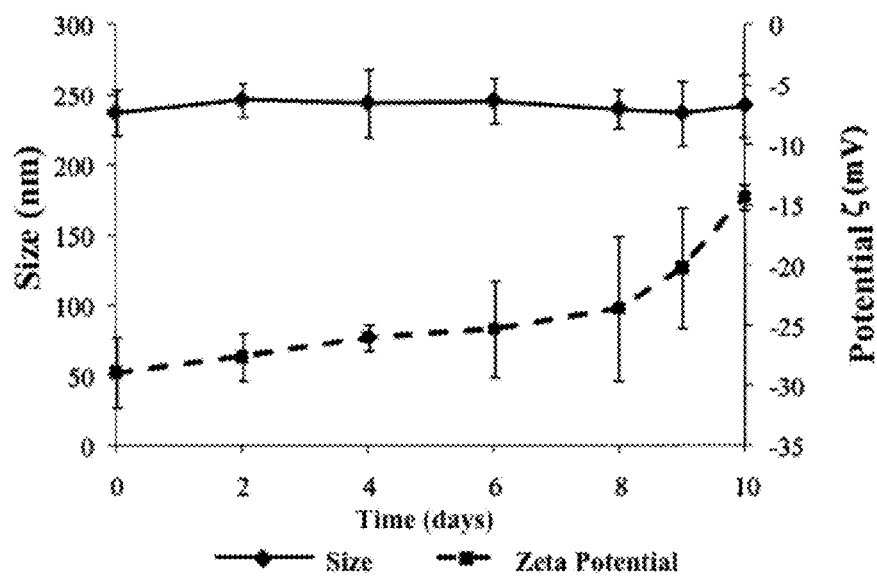

Evaluation of the variation of particle size of the formulation of nanocapsules during storage polyasparagine polyasparagine nanocapsules were prepared, having an oily core composed of lecithin, Miglyol™ 812 and the cationic surfactant benzalkonium chloride (4 mg) or hexadecyltrimethylammonium (4 mg) according to the previously described method. Measurements were taken for particle size over a long period of time, in order to obtain information on the system's evolution over time. Also, the effect of storage temperature (4 and 37° C.) on the stability of nanocapsules was evaluated. The results presented in FIGS. 10a and 10b show the small size variability of the nanocapsules of PAsn, with benzalkonium chloride and hexadecyltrimethylammonium bromide, respectively, during storage.

Example 15

Evaluation of the effect of trehalose and glucose on the particle size of the nanocapsules of PAsn after the lyophilization process Nanocapsules of polyasparagine, an oily core composed of lecithin, Miglyol™ 812 and the cationic surfactant hexadecyltrimethylammonium bromide (1.8 mg) were prepared according to the previously described method. The cryoprotectant effect of the trehalose was evaluated during lyophilization of PAsn nanocapsules and the subsequent recovery of particle size after resuspension, by testing two concentrations of cryprotector, 5 to 10% w/v. We also evaluated the influence of the concentration of nanocapsules (0.25, 0.5 and 1% w/v) in the suspension to be lyophilized. The results in Table 32 show the particle size of the nanocapsules of PAsn after resuspension.

TABLE 32

| [NC] % | [CRIO] % | Size | SD |
|---|---|---|---|
| GLUCOSE | | | |
| 0.125 | 0.25 | 342.7 | 8.856 |
| 0.125 | 1 | 293.5 | 7.862 |
| 0.25 | 0.5 | 302.6 | 8.271 |
| 0.5 | 0.5 | 322.9 | 6.795 |
| 0.5 | 1 | 314.8 | 7.808 |
| TREHALOSE | | | |
| 0.125 | 0.25 | 352.2 | 9.419 |
| 0.125 | 0.5 | 238.3 | 0.459 |
| 0.125 | 1 | 260.4 | 1.752 |
| 0.25 | 0.25 | 269.1 | 26.41 |
| 0.25 | 0.5 | 245.4 | 1.419 |
| 0.25 | 1 | 236.1 | 3.045 |
| 0.5 | 0.25 | 380.5 | 20.22 |
| 0.5 | 0.5 | 258 | 4.07 |
| 0.5 | 1 | 236.5 | 2.285 |

Example 16

Study of the capacity to inhibit cell proliferation of nanocapsules

Figure 11A:
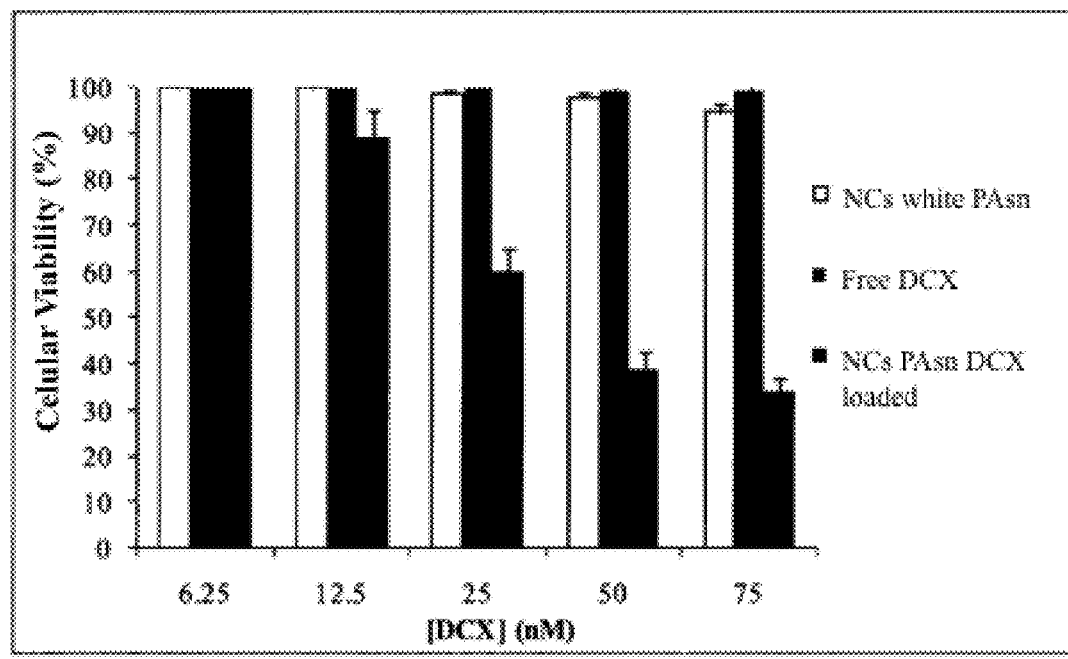
FIG. 11: Viability of cancer cell line NCI-H460 after two (11.a) and 48 (11.b) hours in contact with polyasparagine nanocapsules (NCs PAsn) white, docetaxel (DCX) in solution, and polyasparagine nanocapsules containing docetaxel, for different concentrations of the antitumaral agent. The cationic surfactant used in preparing the nanocapsules was hexadecyltrimethylammonium bromide.
Figure 11B:
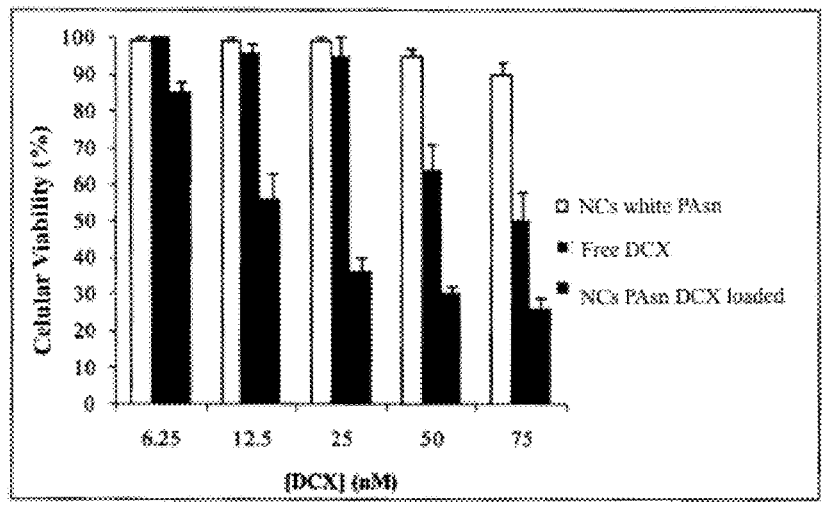

In order to evaluate the potential of Pasn nanocapsules encapsulating docetaxel to inhibit cell proliferation of lung cancer cell line NCI-H460, PAsn nanocapsules were prepared using hexadecyltrimethylammonium bromide (1.8 mg) according to the procedure described in Example 12. The results in FIG. 11 show the greatest ability to inhibit the proliferation of nanocapsules encapsulating docetaxel compared to the free molecule when systems are brought into contact for 2 to 48 h with the cancer cells. Moreover, one can see the safety of the systems without docetaxel. IC50 values were calculated using Graph Pad Prism 2.1 (Graph Pad Software). Thus, the solution of docetaxel showed IC50 values of 105 nM and 36 nM when in contact with the cells for 2 to 48 respectively, while the formulations of PAsn nanocapsules encapsulating docetaxel showed values of about 30 and 13 nM in the same Incubation times, the docetaxel nanoencapsulation being 3.5 and 2.8 times more effective at inhibiting cell proliferation.

Example 17

Figure 12A:
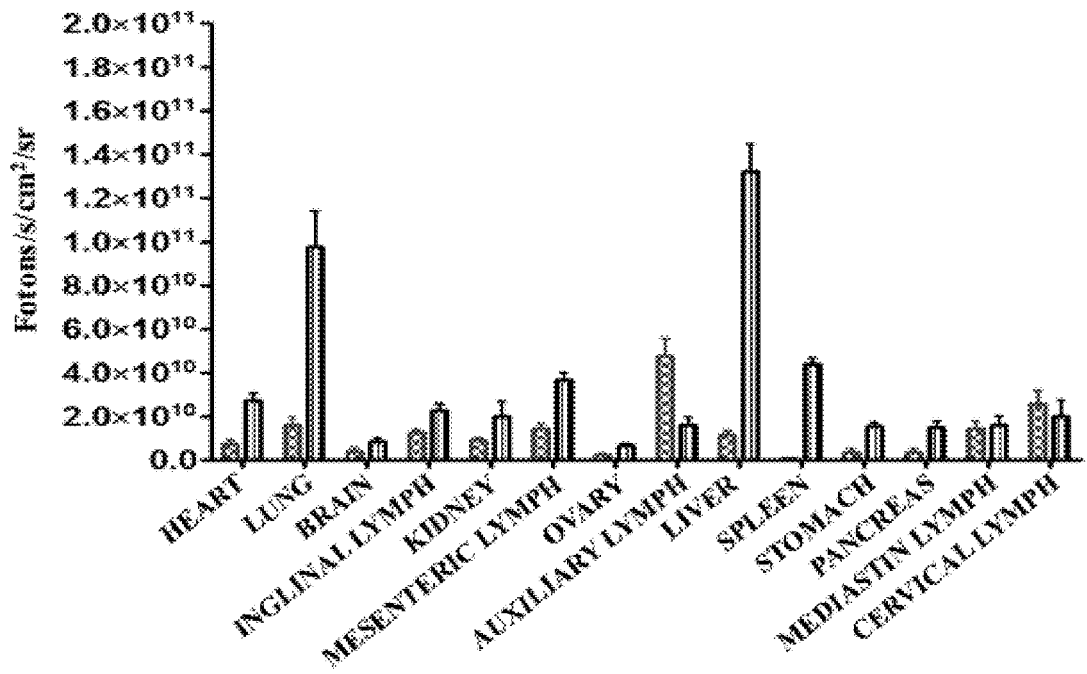
FIG. 12: Fluorescence concentration expressed as fotons/s/cm$^2$/sr in different organs and tissues after administration of polyglutamic-polyethyleneglycol acid nanocapsules of 100 nm, after different time periods: (a) 6 hours, (b) 24 hours, © 48 hours ( ▓▓▓ subcutaneous administration, ▓▓ intravenous administration).
Figure 12B:
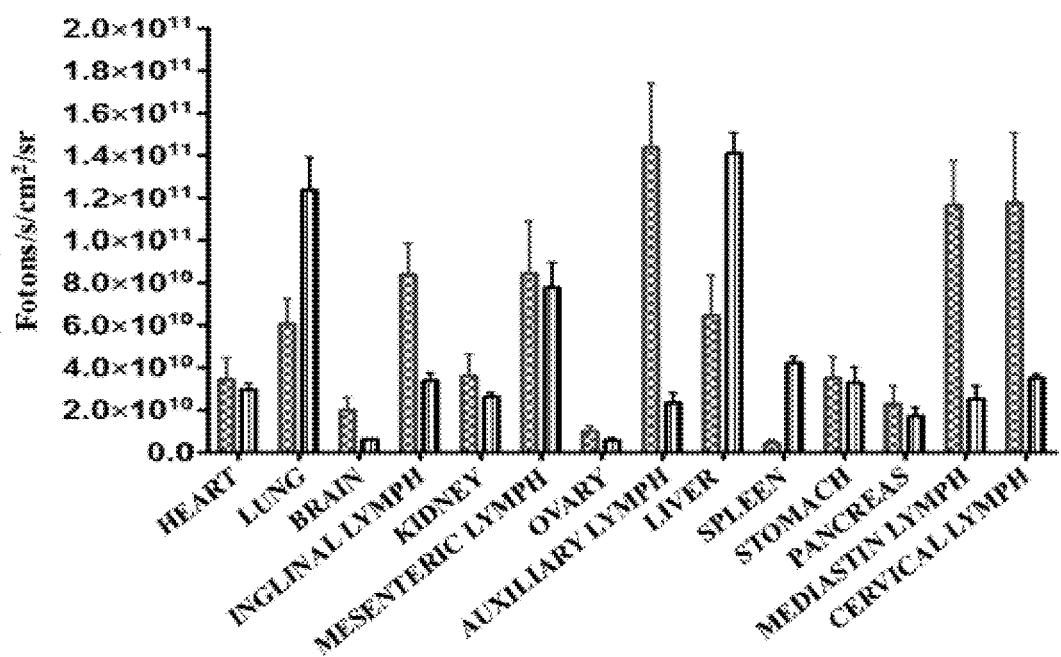
Figure 12C:
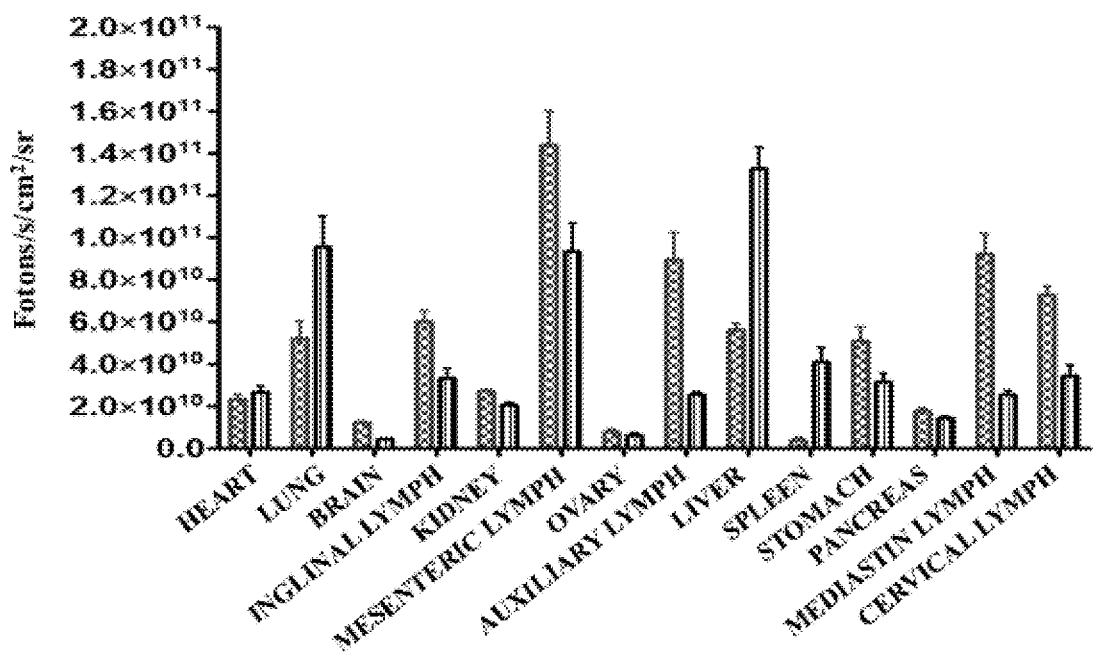
Figure 13A:
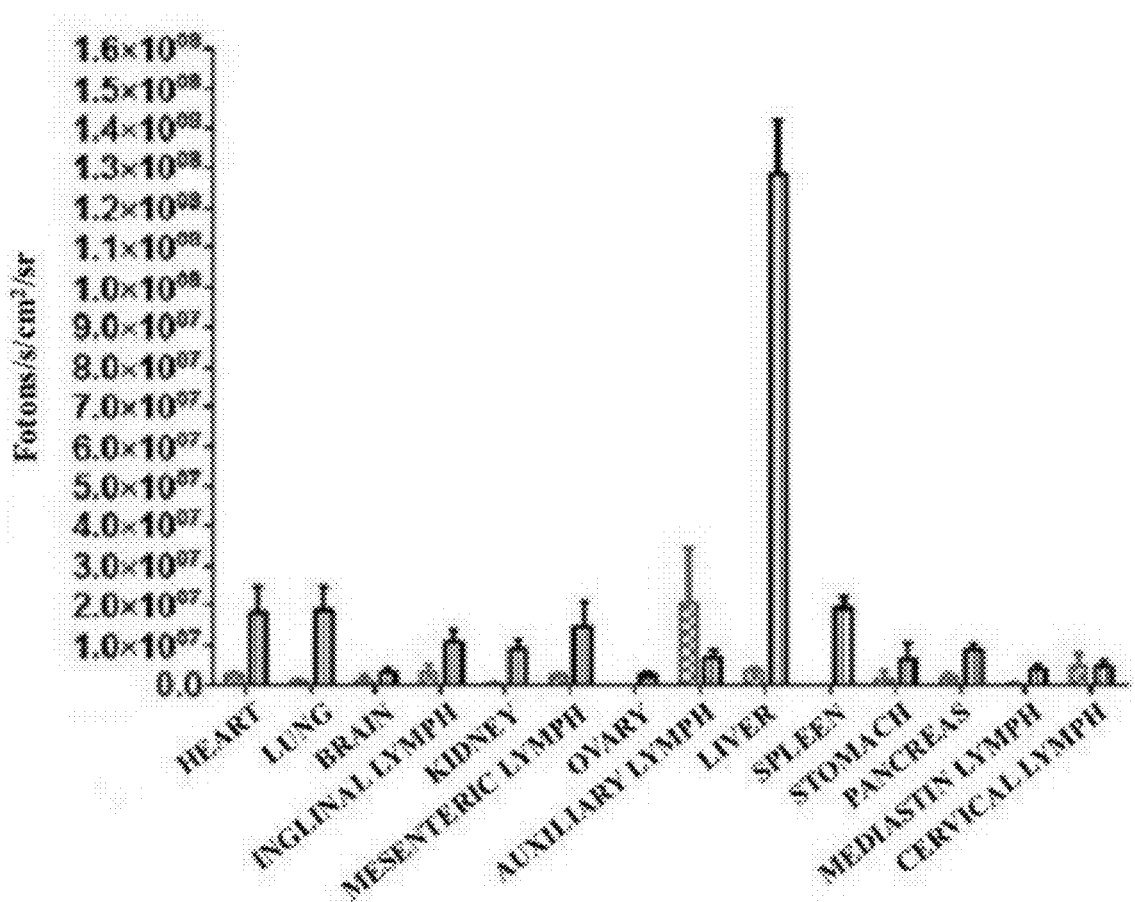
FIG. 13: Fluorescence concentration expressed as fotons/s/cm$^2$/sr in different organs and tissues after administration of polyglutamic-polyethyleneglycol acid nanocapsules of 200 nm, after different time periods: (a) 6 hours, (b) 24 hours, © 48 hours ( ▓▓▓ subcutaneous administration, ▓▓ intravenous administration).
Figure 13B:
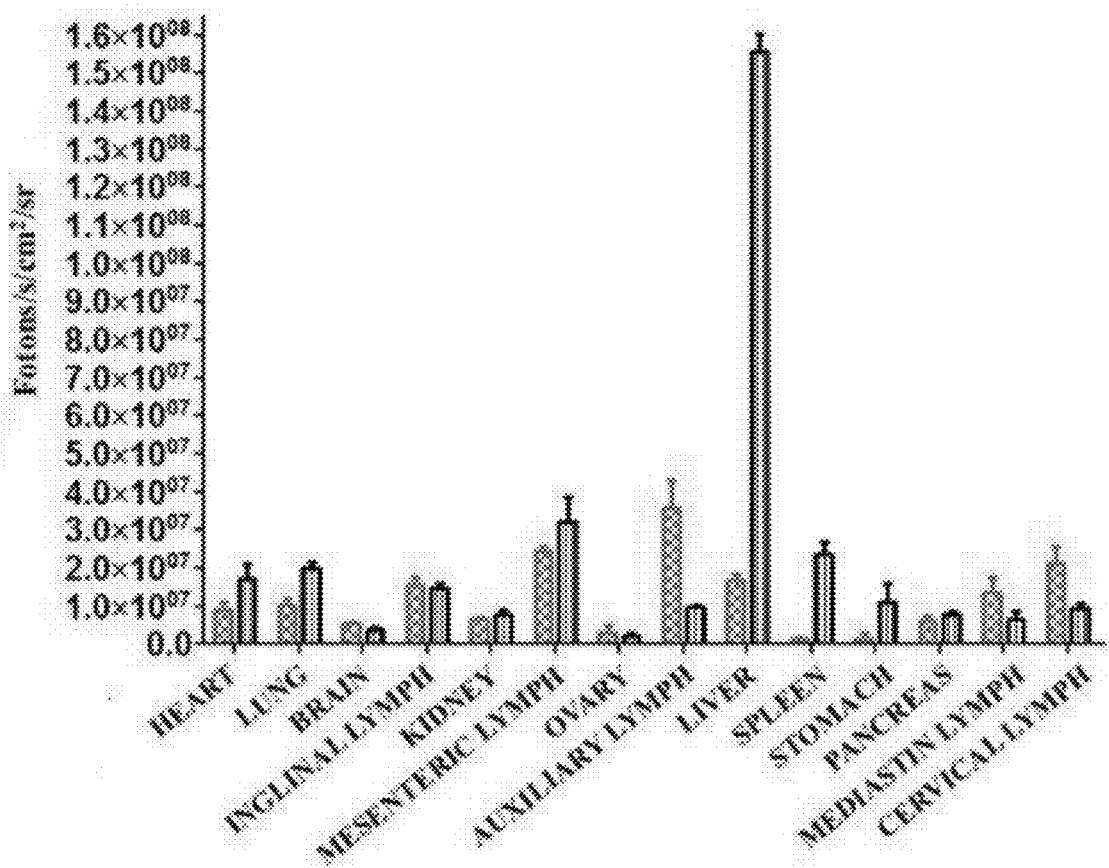
Figure 13C:
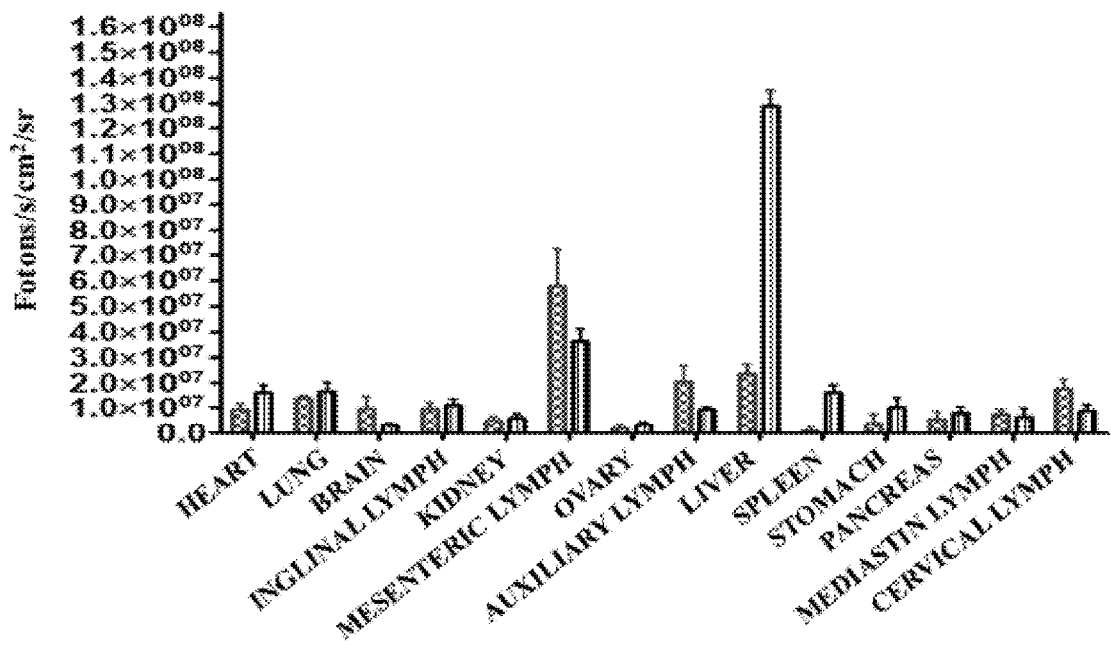

Evaluation of the polyglutamic-polyethyleneglycol acid nanocapsule's biodistribution Nanocapsules of a medium size of 100 nm were prepared according to the solvent diffusion process in one step having a shell of polyglutamic-polyethyleneglycol acid (PGA-PEG) as a sodium salt with a molecular weight of 35,000 Da, a 60% pegylation and a chain size of PEG of 20,000 Da; an oily core made of lecithin, Miglyol™ 812, hexadecyltrimethylammonium bromide. Also, nanocapsules with a mean size of 200 nm were prepared according to the same procedure consisting of a shell of polyglutamic-polyethyleneglycol acid (PGA-PEG) as the sodium salt of 35,000 Da, with a percentage of 60% Pegylation and PEG chain size of 20,000 Da, poloxamer 188 and an oily core composed of lecithin, Miglyol™ 812 and benzalkonium chloride. The size of the nanocapsules could be modulated to achieve such sizes, by suitably modifying the amounts of components and the method of addition of the organic phase over the aqueous phase. For later viewing and quantifying, the nanocapsules were labeled with the lipophilic fluorescent marker DiD (1,1'-dioctadecyl-3,3,3',3'-tetramethylindodicarbocyanine perchlorate). Then, the two formulations of nanocapsules of 100 and 200 nm were isolated and diluted in a solution of 10% trehalose in water and administered subcutaneously (interscapular area) and intravenous (into tail vein) to SCID healthy mice in order to evaluate its biodistribution, with special attention to their accumulation in lymphoid tissues. The injection volume was 100 µl, and nanocapsules concentrations of 100 and 200 nm was 12 mg/ml and 13.6 mg/ml, respectively. In both cases DiD concentration was 11.7 µg/ml. Fluorescence intensity was evaluated in different organs by In Vivo Imaging System (IVIS™ Spectrum, Caliper Life Sciences) at 6, 24 and 48 hours after administration. FIGS. 12 and 13 show the distribution profiles of the fluorescence associated with the nanocapsules of 100 and 200 nm, respectively. More specifically FIGS. 12a, 12b, and 12c show the fluorescence levels (expressed in fotons/s/cm$^2$/sr) in various organs and tissues after administration of polyglutamic-polyethyleneglycol acid (PGA-PEG) of 100 nm, after different periods of time: (a) 6 h, (b) 24 hours, (c) 48 hours (▨ subcutaneous administration, ▥ intravenous administration). Similarly, FIGS. 13a, 13b and 13c show the fluorescence levels (expressed in fotons/s/cm$^2$/sr) in various organs and tissues after administration of polyglutamic-polyethyleneglycol acid (PGA-PEG) nanocapsules of 200 nm, after various periods time: (a) 6 h, (b) 24 hours, (c) 48 hours and (▨ subcutaneous administration, ▥ intravenous administration). Overall, the results show the high lymphatic accumulation of fluorescence associated to the nanocapsules after administration in both ways, this being more pronounced for subcutaneous administration. In fact, after subcutaneous administration, marker vehiculization into the lymphatic system becomes apparent. This lymphatic accumulation is associated with a diminished accumulation in organs responsible for disposal, such as liver and spleen.

Example 18

Study of plasmatic disposal speed of PAsn, PGA and PGA-PEG nanocapsules after I.V. administration in mice Nanocapsules were prepared with different polymers including PAsn, PGA or PGA-PEG by means of the technique in one step described in Example 1.1 and 11.1. These systems were loaded with the fluorescent marker DiD (1,1'-dioctadecyl-3,3,3',3'-tetramethylindodicarbocyanine perchlorate) (concentration of DiD was 100 µg/ml in nanocapsules) prior to administration to Swiss mice (9-12 weeks old, 20-22 g). As control formulation an anionic nanoemulsion loaded with the same marker and at the same concentration was used. Also, a control experiment was performed to determine the residual fluorescence of plasma from blood samples of mice to which 150 µl of saline was administered.

The fluorescent formulations, nanoparticles and nanoemulsion, and the saline control sample were administered by IV injection into mice tails in a volume of 150 µl. At certain time intervals (30 min, 1 h, 3 h and 24 h), blood samples were taken in triplicate by cardiac puncture. The samples were centrifuged for 10 min at 2000 g in Vacutainer tube (SST II Advance, 5 ml, Becton Dickinson France SAS, France). For determination of the fluorescence at time zero, fluorescent nanoemulsion and nanocapsules aliquots were mixed with blood at an adequate rate to simulate the in vivo concentration at time zero (150 µl of formulation in a weight of blood corresponding to 7.5% of the total animal weight, i.e. approximately 150 µl in 1.89 g of blood). Finally, 150 µl of the supernatant samples were placed in a 96 well plate, to proceed to the determination of fluorescence using an Ascent fluorimeter by means of the Fluorscan software (Thermo Fischer Scientific, France). Fluorescence determinations were performed at the excitation wavelength of DiD of 644 nm and emission of 664 nm. The concentration of fluorescence in the blood was calculated assuming a total blood weight in the mice corresponding to 7.5% of the total animal weight.

The fluorescence is expressed in fluorescence units (FU) and is calculated by the following equation:

$$(FU) \text{ sample}-(FU) \text{ of the plasma}$$

Figure 14:
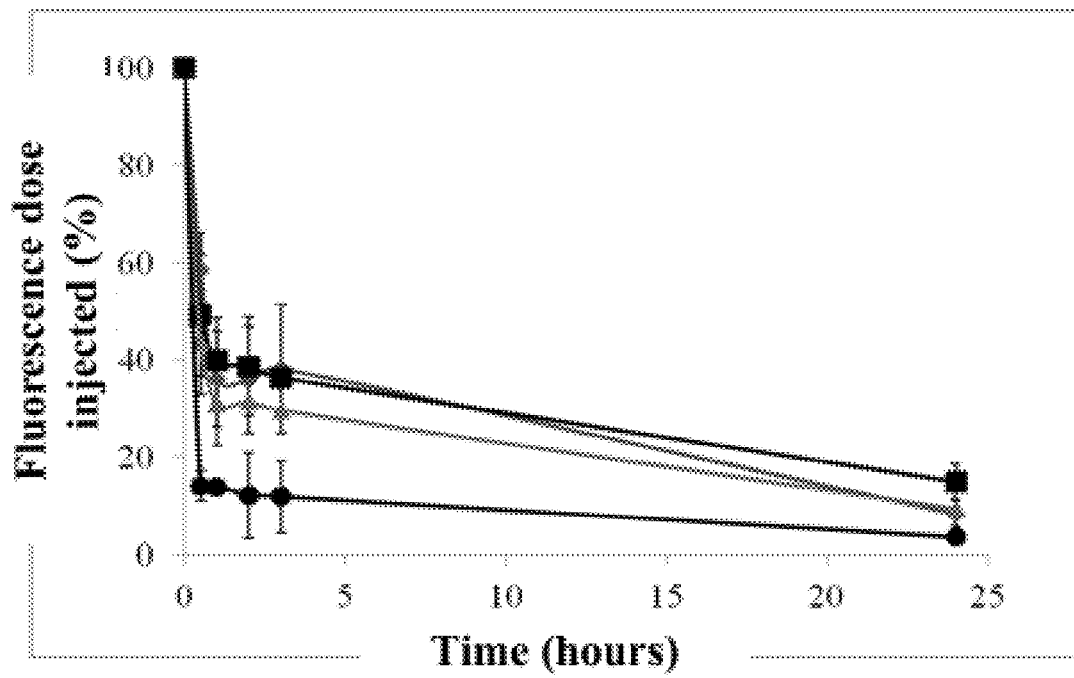
FIG. 14: Elimination kinetics in plasma of the fluorescence associated to the PAsn (▲), PGA (♦) and PGA-PEG (■) nanocapsules after intravenous administration to Swiss rats. Percentage of the injected doses (concentration of DiD in mg/kg of animal's total weight at each moment in relation to the concentration at time zero) is expressed as a function of time. Nanoencapsulation (•) was used as control. Each point represents the mean of the percentage of the injected dose in a group, and is expressed as n=3±D.E.

FIG. 14 shows the percentage of fluorescence dose injected (DiD concentration in mg/kg of the total weight of the animal at each time in relation to the concentration at time zero) remaining in plasma after different periods of time after intravenous injection in Swiss mice. 100% of the fluorescence corresponds to the fluorescence at time zero. FIG. 1 shows, therefore, the plasma elimination kinetics of fluorescence associated to PAsn, PGA and PGA-PEG nanocapsules after administration. The anionic nanoemulsion was used as control. Each point represents the mean percentage of the injected dose in a group n=3±SD.

The results shown in FIG. 14 show the differences in plasma clearance rate of the various formulations evaluated.

A significant reduction in the removal rate of the fluorescence associated to nanocapsule formulations can be observed, compared to that for the nanoemulsion control. This highlights the importance of the polymeric shell in order to prolong the blood residence time of formulations. This increased residence time in the blood is critical in preventing the undesirable buildup of the systems in organs, while facilitating access to tumor tissue.

To obtain a more accurate comparison of the plasma elimination kinetics of the nanocapsules it is proceeded to obtain pharmacokinetic parameters through a non-compartmental model using the statistical package Kinetica 5.1 (Thermo Fisher Scientific, France) (Table 1).

The half-life ($t_{1/2}$) distribution or disposal is calculated by the following formula:

$$t_{\frac{1}{2}} = \frac{\log(2)}{Lz}$$

Lz being the slope corresponding to the linearization of each phase of the plasma level-time curve. Lz was determined by linear regression using predefined intervals (half-life for the distribution [0-1 h] and the $t_{1/2}$ elimination [1-24 h] respectively). For determining the area under the curve (AUC) the standard trapezoidal model was used during experimental time (AUC [0-24 hr]) without extrapolation as well as for AUMC. The mean residence time in the body (MRT) was calculated from 0 to 24 h, according to the equation:

$$MRT\,[0\text{-}24\text{ h}] = \frac{AUMC\,[0\text{-}24\text{ h}]}{AUC\,[0\text{-}24\text{ h}]}$$

Table 1 shows the values for the parameters: the half-life of distribution (alpha phase) ($t_{1/2}\,\alpha$, hours), calculated from 0 to 1 hours, the half-life of elimination (beta) ($t_{1/2}\,\beta$, hours) calculated from 1 to 24 hours, the mean residence time (MRT, hours) calculated from 0 to 24 hours and area under the plasma level/time curve (AUC, hours) calculated from 0 to 24 hours. The results obtained for these parameters show the differences in plasma elimination kinetics of the different formulations. There is a considerable improvement of the parameters obtained for all formulations of nanocapsules compared to those obtained for the nanoemulsion without polymer coating (formulation control). The overall conclusion of these results is the prolonged plasma residence of all nanocapsules, a very favorable behavior for vehiculizating active ingredients to tumor sites.

TABLE 1

Pharmacokinetic parameters of PGA, PGA-PEG, PAsn nanocapsules and nanoemulsion used as a control after IV administration in mice.

| Formulation | $t_{1/2\,\alpha}$(h) (0-1 h) | $t_{1/2}\,\beta$(h) (1-24 h) | MRT (h) (0-24 h) | AUC (mg/ml*h) (0-24 h) |
|---|---|---|---|---|
| PGA Nanocapsules | 0.66 | 10.02 | 9.72 | 38.02 |
| PGA-PEG Nanocapsules | 0.74 | 16.08 | 17 | 50.65 |
| PAsn Nanocapsules | 0.58 | 12.64 | 12.75 | 34.83 |
| Nanoemulsion | 0.34 | 8.17 | 6.59 | 11.43 |

Example 19

Study of the antitumor efficacy of the nanocapsules of PAsn and PGA-PEG loaded with docetaxel evaluated in an in vivo model of U87MG glyoma in mice after intravenous injection In order to evaluate the potential of the nanocapsules of PGA-PEG and PAsn loaded with docetaxel to inhibit tumor growth in an in vivo model of a U87MG tumor implanted in mice, the corresponding nanocapsules were prepared according to examples 1.1 and 11.1. Also, such efficacy was compared with that of the commercial formulation Taxotere™.

For tumor growth, the animals (NMRI-nu naked athymic mice 6 weeks old, 20-24 g) were anesthetized with a mixture of isoflurane/oxygen and then subcutaneously injected into the right flank with a suspension of $1\times10^6$ U87MG cells (ATCC, Manassas, Va.) in 150 µl of HBSS. Tumor growth was evaluated by measuring the tumor with a Vernier caliber every 3 days. Tumor volume (V) has been estimated using the following formula:

$$V = \left(\frac{\pi}{6}\right) \times (\text{width})^2 \times (\text{length}).$$

When the tumor reached a size of 200 mm³ the mice were divided into 4 groups who were given different treatments (PAG-PEG nanocapsules, PAsn nanocapsules, the nanoemulsion commercial control formulation and Taxotere®). For each treatment the dose of docetaxel administered by IV injection was 2 mg of docetaxel/kg animal weight. Maximum formulation volume injected was 150 µL. The control group was given the same volume of saline. Tumor size was measured two times per week for a period of 24 days.

Figure 15A:
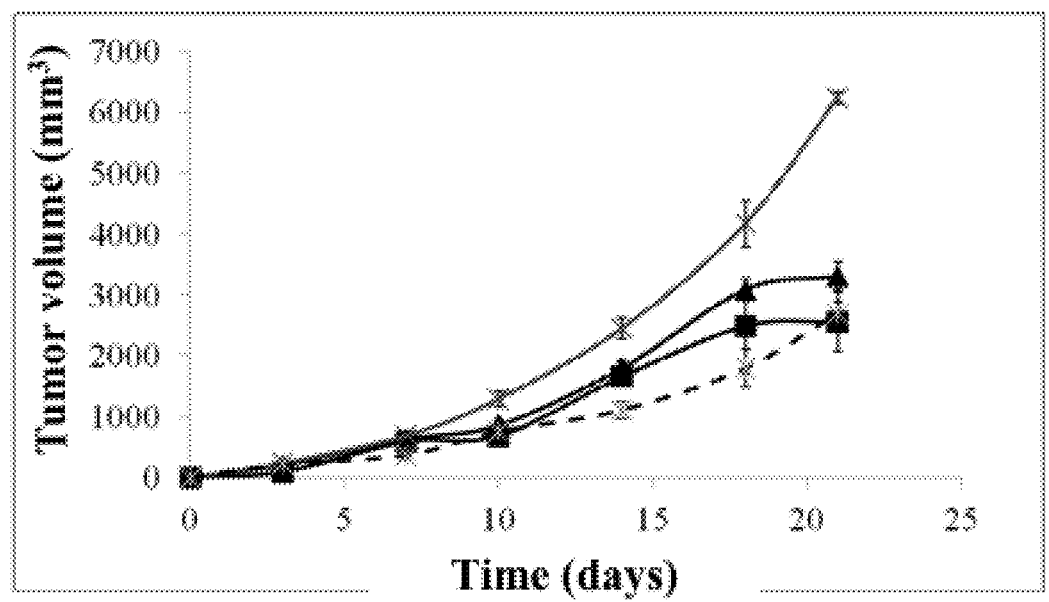
FIG. 15: (a) Evolution of tumor size in time after administration of PAsn (▲), PGA-PEG (♦), Taxotere™ (--X--) and saline solution (X) in rats (subcutaneous glyoma tumoral model U87MG); (b) tumor volume growth, relative to initial volume, in rats after 18 and 21 days, after injection of the different formulations. Taxotere™ and physiologic saline solution were used as controls. Statistical analysis shows the significant differences in tumor size on day 18 and day 21 in the animals treated with the nanocapsule formulations and with Taxotere™ in relation to controls ($*P<0.05$ $**P<0.01$—F test ANOVA).
Figure 15B:
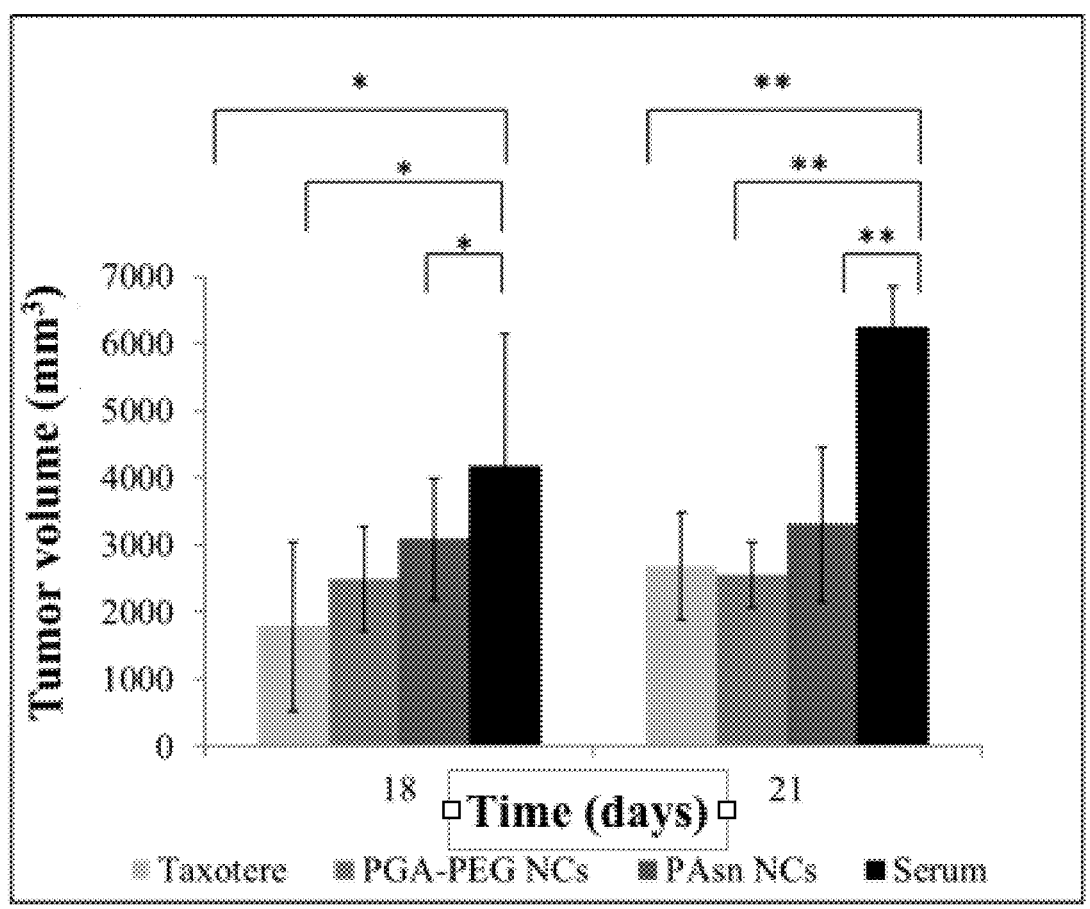

FIG. 15a shows the evolution of the increase of tumor volume (the size difference between each time and the initial size) of the animals treated with the drug-loaded nanocapsules and Taxotere™ and with the saline control. The first results indicate that the docetaxel retains antitumor activity in vivo when encapsulated. Furthermore, nanocapsule formulations were as effective as the commercial formulation, being both formulations effective in terms of reduction of tumor growth rate. Similarly, FIG. 15b shows the increase in tumor volume after 18 and 21 days compared to the size at time zero. It can be appreciated that the differences in tumor size of the treated and untreated animals (serum was administered) were significant for the two times. This analysis reflects the efficacy test of the concept of nanocapsule formulations developed.

Figure 16:
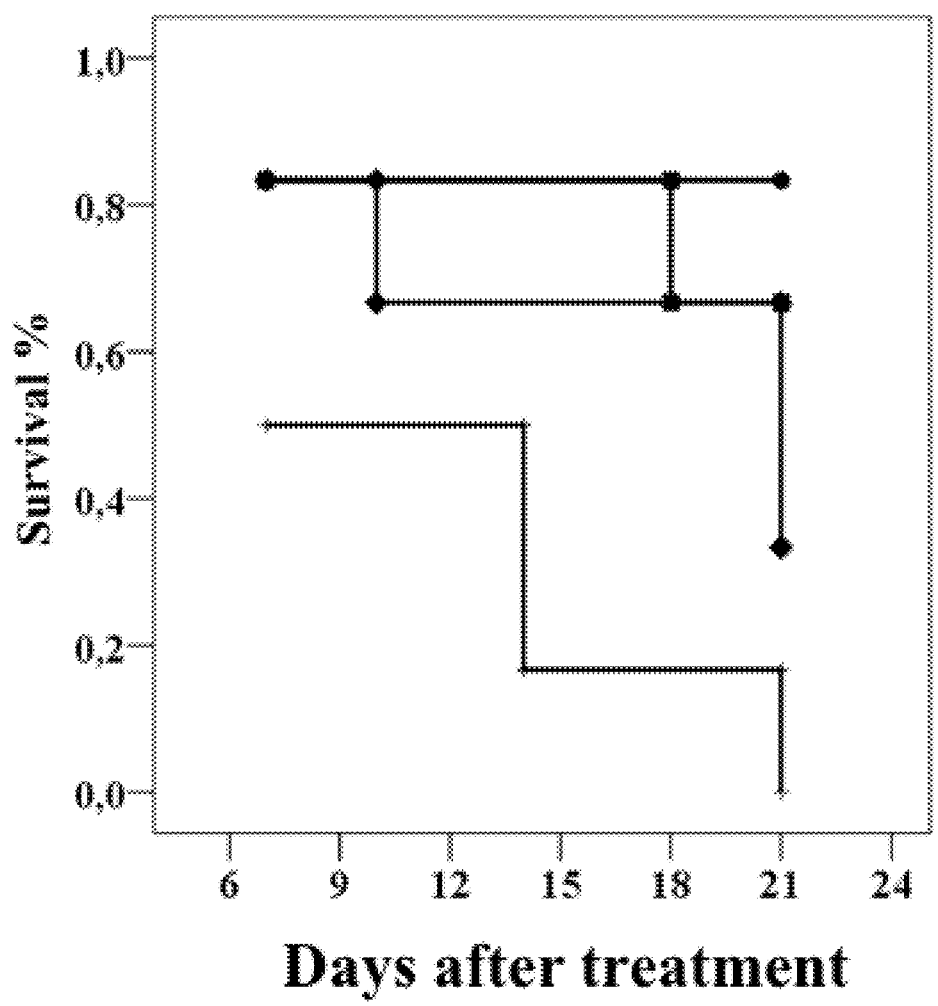
FIG. 16: Kaplan-Meier survival curves of animals treated with the different nanocapsules loaded with docetaxel (PAsn (•), PGA-PEG (■), Taxotere™ (♦) and saline solution (+)) in comparison to those obtained after administration of Taxotere™ and physiologic saline solution.

FIG. 16 shows the percentage of mice surviving after different periods of time and after being subjected to different treatments, according to the Kaplan-Meier method. The results show a much higher survival rate in the case of mice treated with the formulations of nanocapsules (60-80% survival) than with Taxotere™ (30% survival). This reduction in drug toxicity of nanocapsules is to be attributed to higher selectivity of the treatment, which is consistent with prolonged circulation time in plasma of nanocapsules.

The above results were also analyzed in terms of mean and median survival time after tumor implantation. Table 2 shows the survival time of the animals expressed as range (difference between the longest and shortest time), the arithmetic mean and standard deviation (SD) of the mean survival time and the median. Also, Table 2 shows the percentage of the increase in survival (% IST) calculated from the values of the mean or median. For example, in the case of mean, the calculation would be made according to the equation:

$$\% \, IST = \frac{\text{Media}_T - \text{Media}_C}{\text{Media}_C} \times 100$$

Where Media$_T$ represents the mean survival of the treated animals and Media$_C$ represents the mean survival of untreated animals (saline administration).

The table also shows the statistical probability (p) associated with the differences in the parameter "mean survival time" for each of the formulations compared to the control ($p<0.05$ was considered statistically significant.) Statistical differences were calculated using the log-rank test (Mantel-Cox test). The results of survival of the treated animals show the superiority of the nanocapsule formulations compared to Taxotere™.

TABLE 2

Mean survival time of treated animals with the different formulations of docetaxel loaded nanocapsules, compared to those obtained after administration of Taxotere ™ and the saline control.

| Treatment | N | Range | Survival Time (days) Median | Mean ± SD | IST median | IST mean | Increase in survival time (%) p-value vs serum |
|---|---|---|---|---|---|---|---|
| PAsn Nanocapsules | 6 | 7-18 | 0 | 18.1 ± 2 | 0 | 61.6 | 0.066 |
| PGA-PEG Nanocapsules | 6 | 14-21 | 0 | 18.7 ± 2 | 0 | 66.96 | 0.036 |
| Taxotere ™ | 6 | 7-21 | 21 | 16.8 ± 2 | 50 | 50 | 0.147 |
| Saline serum | 6 | 7-14 | 14 | 11.2 ± 2 | — | — | |

% IST percentage of survival with respect to control.

The invention claimed is:

1. A system for the administration of active ingredients comprising nanocapsules having a core comprising an oil and a cationic surfactant and a shell comprising a polymer selected from the group consisting of polyglutamic acid (PGA), polyglutamic-polyethyleneglycol acid (PGA-PEG), hyaluronic acid (HA), polyasparagine (PAsn), wherein the polyasparagine has approximately 5% of aspartic acid residues, and combinations thereof, and optionally an active ingredient, with the proviso that when said nanocapsules system includes polyglutamic acid or polyglutamic-polyethyleneglycol acid (PGA-PEG), then the active ingredient is not a didemnin or tamandarin, wherein the nanocapsules have a negative zeta potential ranging from −0.5 mV to −69 mV when measured in a dispersion of the nanocapsules in water.

2. The system according to claim 1, wherein the cationic surfactant is selected from the group consisting of benzalkonium chloride, benzethonium chloride, cetylpyridinium chloride, cetyltiridinium bromide, dodecyltrimethylammonium bromide, trimethyltetradecylamonium bromide, hexadecyltrimethylammonium bromide and poloxamines, and mixtures thereof.

3. The system according to claim 1, wherein the oil is selected from the group consisting of animal oils, fish oils, vegetable oils, mineral oils and silicone oils, and synthetic and semisynthetic derivatives thereof, and combinations thereof.

4. The system according to claim 1, additionally comprising an oil-soluble surfactant.

5. The system of claim 4 wherein the oil soluble surfactant is a phospholipid selected from the group consisting of lecithin, phosphatidylglycerol, phosphatidylserine, phosphatidylinositol, diphosphatidylglycerol, phosphatidic acid, phosphatidylcholine and phosphatidylethanolamine.

6. The system according to claim 1 additionally comprising a water-soluble surfactant.

7. The system of claim 6 wherein the water-soluble surfactant is selected from the group consisting of poloxamer and polysorbates.

8. The system of claim 7, wherein said poloxamer is poloxamer 188.

9. The system according to claim 1, wherein the active ingredient is selected from the group consisting of peptides, proteins, lipids or lipophilic compounds, saccharide compounds, nucleic acids and nucleotide compounds or combinations thereof.

10. The system of claim 9, wherein the active ingredient is docetaxel.

11. The system according to claim 9, wherein the active ingredient is selected from the group consisting of an oligonucleotide, RNA interference, a DNA plasmid or a polynucleotide.

12. The system according to claim 1, characterized in that the system is in lyophilized form.

13. A pharmaceutical composition comprising the system defined in claim 1.

14. The pharmaceutical composition according to claim 13, wherein said composition is for topical, parenteral, or mucosal administration.

15. The pharmaceutical composition as defined in claim 13, wherein the composition is for the treatment of cancer.

16. The product of the process comprising the steps of (a) preparing an aqueous solution comprising a polymer selected from the group consisting of polyglutamic acid (PGA), polyglutamic-polyethyleneglycol acid (PGA-PEG), hyaluronic acid (HA), polyasparagine (PAsn), wherein the polyasparagine has approximately 5% of aspartic acid residues, and combinations thereof, and optionally a water-soluble surfactant; (b) preparing an organic solution comprising an oil and a cationic surfactant, and optionally an oil-soluble surfactant; (c) mixing under stirring the solutions prepared in steps (a) and (b), spontaneously obtaining nanocapsules having a shell and core, and (d) optionally, wholly or partially evaporating to constant volume the organic solvents from the mixture obtained in the previous stage, wherein the nanocapsules have a negative zeta potential ranging from −0.5 mV to −69 mV when measured in a dispersion of the nanocapsules in water.

17. The product of the process of claim 16, further comprising the step of adding an active ingredient selected from the group consisting of peptides, proteins, lipids or lipophilic compounds, saccharide compounds, nucleic acids and nucleotide compounds or combinations thereof, to the aqueous solution, the organic solution or the nanocapsules, with the proviso that when said polymer comprises polyglutamic acid or polyglutamic-polyethyleneglycol acid (PGA-PEG), then the active ingredient is not a didemnin or tamandarin.

18. The system of claim 16, further comprising the step of lyophilization of the system obtained in the presence of cryoprotectants.

19. The product of the process comprising the steps of coating a nanoemulsion, at least constituted by an oil, a cationic surfactant, optionally an oil-soluble surfactant and an aqueous phase optionally comprising a water-soluble surfactant, through a process of incubation with an aqueous solution comprising a polymer selected from the group consisting of polyglutamic acid, polyglutamic-polyethyleneglycol acid, hyaluronic acid, polyasparagine, wherein the polyasparagine has approximately 5% of aspartic acid residues, and mixtures thereof, to form nanocapsules having a shell and a core, wherein the nanocapsules have a negative zeta potential ranging from −0.5 mV to −69 mV in a dispersion in water.

20. The product of the process of claim 19, further comprising the step of adding an active ingredient selected from the group consisting of peptides, proteins, lipids or lipophilic compounds, saccharide compounds, nucleic acids and nucleotide compounds or combinations thereof, to the nanoemulsion, the aqueous solution, or the nanocapsules, with the proviso that when said polymer comprises polyglutamic acid or polyglutamic-polyethyleneglycol acid (PGA-PEG), then the active ingredient is not a didemnin or tamandarin.

21. The system according to claim 1, wherein the polymer is hyaluronic acid (HA).

\* \* \* \* \*